United States Patent
Yokoi et al.

(10) Patent No.: US 7,993,263 B2
(45) Date of Patent: Aug. 9, 2011

(54) METHOD AND PORTABLE DEVICE FOR DISPLAYING AN IMAGE FROM A CAPSULE TYPE MEDICAL DEVICE

(75) Inventors: Takeshi Yokoi, Hino (JP); Hironobu Takizawa, Hachioji (JP); Hidetake Segawa, Hachioji (JP); Hitoshi Mizuno, Koganei (JP); Hideyuki Adachi, Sagamihara (JP); Hiroki Moriyama, Akishima (JP); Hisao Yabe, Hachioji (JP)

(73) Assignee: Olympus Corporation, Tokyo (JP)

( * ) Notice: Subject to any disclaimer, the term of this patent is extended or adjusted under 35 U.S.C. 154(b) by 279 days.

(21) Appl. No.: 11/186,587

(22) Filed: Jul. 21, 2005

(65) Prior Publication Data

US 2005/0256372 A1 Nov. 17, 2005

Related U.S. Application Data

(63) Continuation of application No. 10/205,513, filed on Jul. 25, 2002, now Pat. No. 6,951,536.

(30) Foreign Application Priority Data

Jul. 30, 2001 (JP) ................................. 2001-229952
Oct. 30, 2001 (JP) ................................. 2001-333125

(51) Int. Cl.
*A61B 1/045* (2006.01)
(52) U.S. Cl. ......................... 600/118; 600/109; 600/160
(58) Field of Classification Search .................. 600/109, 600/160, 118
See application file for complete search history.

(56) References Cited

U.S. PATENT DOCUMENTS

| | | | |
|---|---|---|---|
| 3,683,389 A | | 8/1972 | Hollis et al. |
| 5,029,016 A | * | 7/1991 | Hiyama et al. ................. 358/403 |
| 5,217,003 A | * | 6/1993 | Wilk ............................. 600/109 |
| 5,604,531 A | | 2/1997 | Iddan et al. |
| 5,609,560 A | * | 3/1997 | Ichikawa et al. .............. 600/101 |
| 5,622,528 A | * | 4/1997 | Hamano et al. ............... 600/118 |
| 5,662,587 A | | 9/1997 | Grundfest et al. |
| 5,878,746 A | | 3/1999 | Lemelson et al. |
| 6,184,922 B1 | * | 2/2001 | Saito et al. ...................... 348/65 |
| 6,240,312 B1 | | 5/2001 | Alfano et al. |
| 6,459,176 B1 | | 10/2002 | Brockel et al. |

(Continued)

FOREIGN PATENT DOCUMENTS

DE 100 28 155 A1 12/2000

(Continued)

OTHER PUBLICATIONS

Official Action, mailed Jan. 25, 2001, from the Japan Patent Office in counterpart Japanese Patent Application No. 2001-229952, together with a partial English translation.

*Primary Examiner* — John P Leubecker
(74) *Attorney, Agent, or Firm* — Scully, Scott, Murphy & Presser, P.C.

(57) ABSTRACT

A method of displaying an image in a subject is provided. The method including: capturing an image using a capsule type medical device introduced into the subject; generating a wireless signal of the image; receiving the wireless signal of the image at the outside of the subject with an external device; and displaying the image based on the received signal, on a first display portion contained in the same housing as the external device.

16 Claims, 21 Drawing Sheets

U.S. PATENT DOCUMENTS

| | | | |
|---|---|---|---|
| 6,490,490 B1 * | 12/2002 | Uchikubo et al. | 700/65 |
| 6,529,620 B2 * | 3/2003 | Thompson | 382/141 |
| 6,678,764 B2 * | 1/2004 | Parvulescu et al. | 710/65 |
| 6,709,387 B1 * | 3/2004 | Glukhovsky et al. | 600/109 |
| 6,944,316 B2 | 9/2005 | Glukhovsky et al. | |
| 7,039,453 B2 * | 5/2006 | Mullick et al. | 600/476 |
| 7,160,258 B2 * | 1/2007 | Imran et al. | 600/593 |
| 2001/0043729 A1 | 11/2001 | Giger et al. | |
| 2002/0093814 A1 | 7/2002 | Egli | |
| 2002/0103417 A1 * | 8/2002 | Gazdzinski | 600/109 |
| 2002/0109774 A1 | 8/2002 | Meron et al. | |
| 2002/0171669 A1 | 11/2002 | Meron et al. | |
| 2002/0177779 A1 | 11/2002 | Adler et al. | |
| 2003/0043263 A1 | 3/2003 | Glukhovsky et al. | |

FOREIGN PATENT DOCUMENTS

| | | |
|---|---|---|
| EP | 0 667 115 A1 | 8/1995 |
| JP | 48-037517 | 11/1973 |
| JP | 57-45833 | 3/1982 |
| JP | 4-109927 | 10/1992 |
| JP | 6-285044 | 10/1994 |
| JP | 7-111985 | 5/1995 |
| JP | 7-289504 | 11/1995 |
| JP | 8-79589 | 3/1996 |
| JP | 11-225996 | 8/1999 |
| JP | 2000-342523 A | 12/2000 |
| JP | 2000-342526 | 12/2000 |
| JP | 2001-95755 | 4/2001 |
| JP | 2001-137182 | 5/2001 |
| WO | WO 92/21307 | 12/1992 |
| WO | WO 00/22975 | 4/2000 |
| WO | WO 01/50941 A2 | 7/2001 |
| WO | WO 01/87377 A2 | 11/2001 |
| WO | WO 02/45567 A2 | 6/2002 |
| WO | WO 02/055126 A2 | 11/2002 |

* cited by examiner

FIG.19
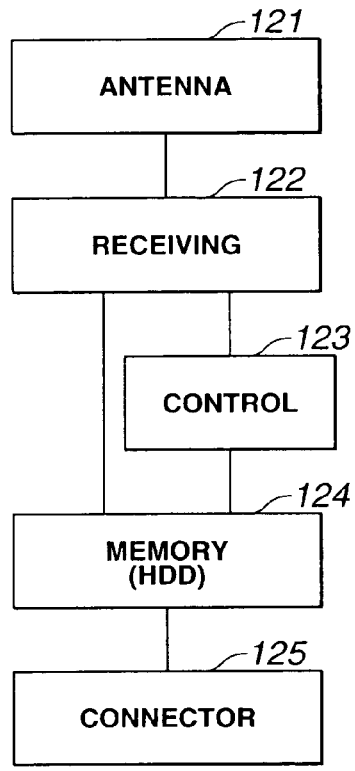
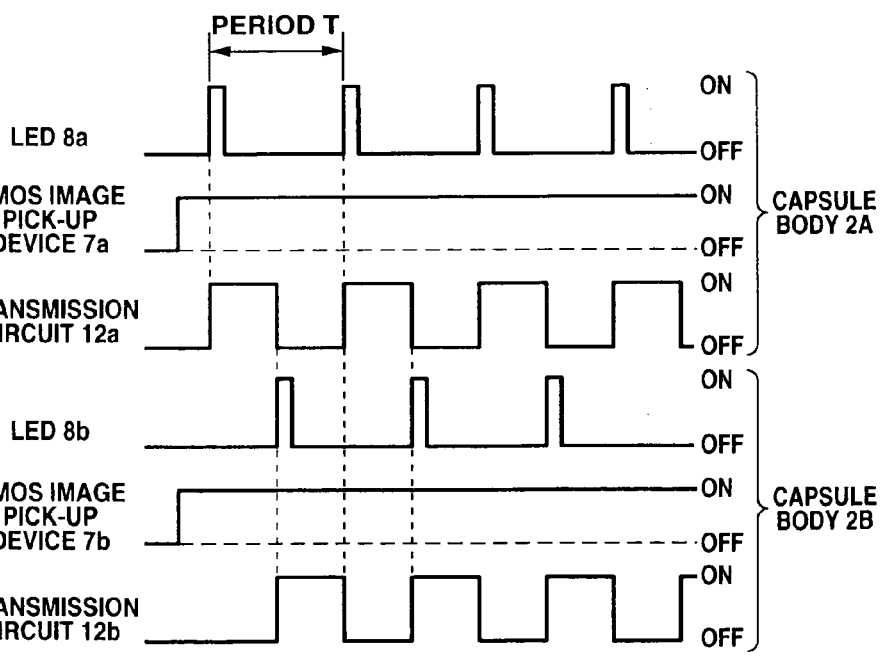

FIG.29
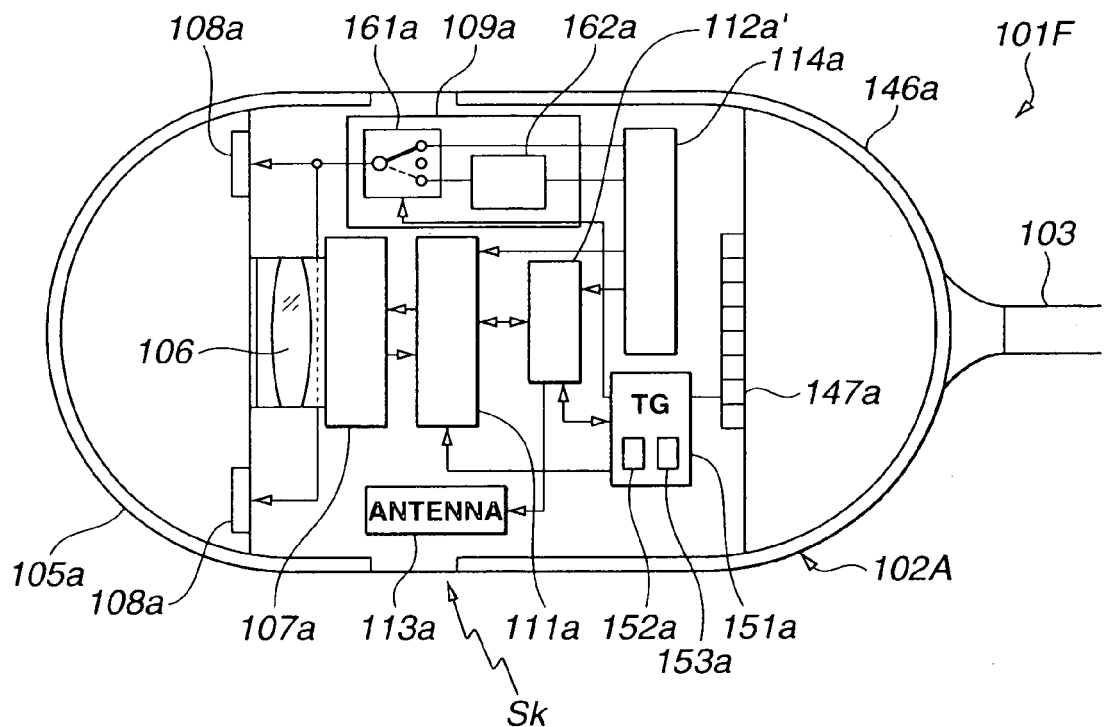
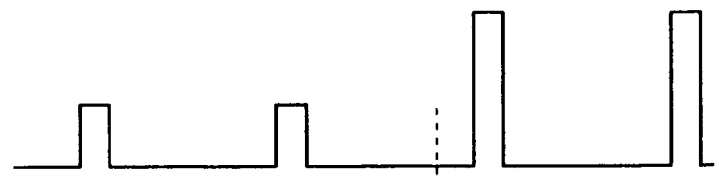
FIG.30A LED
FIG.30B SWITCH OPERATION SIGNAL Sk

METHOD AND PORTABLE DEVICE FOR DISPLAYING AN IMAGE FROM A CAPSULE TYPE MEDICAL DEVICE

CROSS-REFERENCE TO RELATED APPLICATIONS

This application is a continuation of U.S. application Ser. No. 10/205,513, filed Jul. 25, 2002, now U.S. Pat. No. 6,951,536, which claims benefit of Japanese Applications Nos. 2001-229952 filed on Jul. 30, 2001 and 2001-333125 filed on Oct. 30, 2001, the contents of each of which are incorporated by this reference.

BACKGROUND OF THE INVENTION

1. Field of the Invention

The present invention relates to a capsule-type medical device and medical system for conducting, for example, examinations in somatic cavities with a capsule body incorporating an image pickup device.

2. Description of the Related Art

Capsule-type endoscopes, which are used to conduct, for example, examinations by inserting a capsule body shaped as a capsule into somatic cavities and lumens of human being or animals have recently been suggested.

For example, the endoscope disclosed in Japanese Patent Application Laid-open No. H7-111985 comprises a spherical capsule whose shape was split in two.

However, within the framework of such conventional technology, the two capsules were almost of the same size. Therefore, ability of advancing and easiness of swallowing were not sufficiently improved.

Further, endoscopes have recently come into wide use in medical and industrial fields. For example, in case of endoscopic examinations in somatic cavity, an insertion member has to be inserted and the patient's pain is increased. A conventional example of a capsule-type endoscope shaped as a capsule to resolve this problem was disclosed in Japanese Patent Application Laid-open No. 2001-95755.

However, because capsule-type endoscopes capture images while executing unidirectional movement in lumen portions in the body by utilizing peristalsis inside the body, in the conventional example, the images of the entire inner wall of lumen are difficult to be captured without a miss.

On the other hand, Japanese Patent Application Laid-open No. 2000-342526 discloses an endoscope in which illumination and observations means are provided on the front and back ends of a long cylindrical member.

In this case, observations can be conducted with two observation means with different observation directions. Therefore, the drawbacks of the above-described conventional examples can be overcome or eliminated. However, the problem is that because of a long cylindrical shape, the endoscope is difficult to move smoothly through curved portions and the significant patient's pain is increased.

SUMMARY OF THE INVENTION

Accordingly, a capsule-type medical device, which is advanced through a digestive tract of a human being or animal for conducting an examination, therapy, or treatment is provided. The capsule-type medical device comprising: a plurality of capsule bodies; a soft linking unit which links the plurality of capsule bodies and has an outer diameter less than that of any of the capsule bodies; and a joining member which joins two or more of the plurality of capsule bodies in a prescribed position.

Also provided is a method for examination, therapy, or treatment of the digestive tract of a human being by using a capsule-type medical device comprising a plurality of capsule bodies. The method comprising: swallowing the capsule-type medical device in a linear shape; advancing the capsule-type medical device entirely through the narrow lumen portion of the digestive tract; and joining at least two of the plurality of capsule bodies in the prescribed position at a predetermined portion of the digestive tract.

BRIEF DESCRIPTION OF THE DRAWINGS

FIG. 19 is a block-diagram illustrating a modification example of the configuration of the external unit of the fourth embodiment;

FIGS. 20A to 20F are timing charts of illumination and image capturing conducted when the external unit shown in FIG. 19 was used;

FIG. 29 illustrates a part of internal configuration of the capsule-type endoscope of the sixth embodiment of the present invention;

FIG. 30A and FIG. 30B are timing charts for explaining the operation of controlling the intensity of light emission by an external signal, according to the sixth embodiment of the present invention;

The above and other objects, features and advantages of the invention will become more clearly understood from the following description referring to the accompanying drawings.

DESCRIPTION OF THE PREFERRED EMBODIMENTS

The embodiments of the present invention will be explained hereinbelow with reference to the accompanying drawings.

First Embodiment

Figure 1:
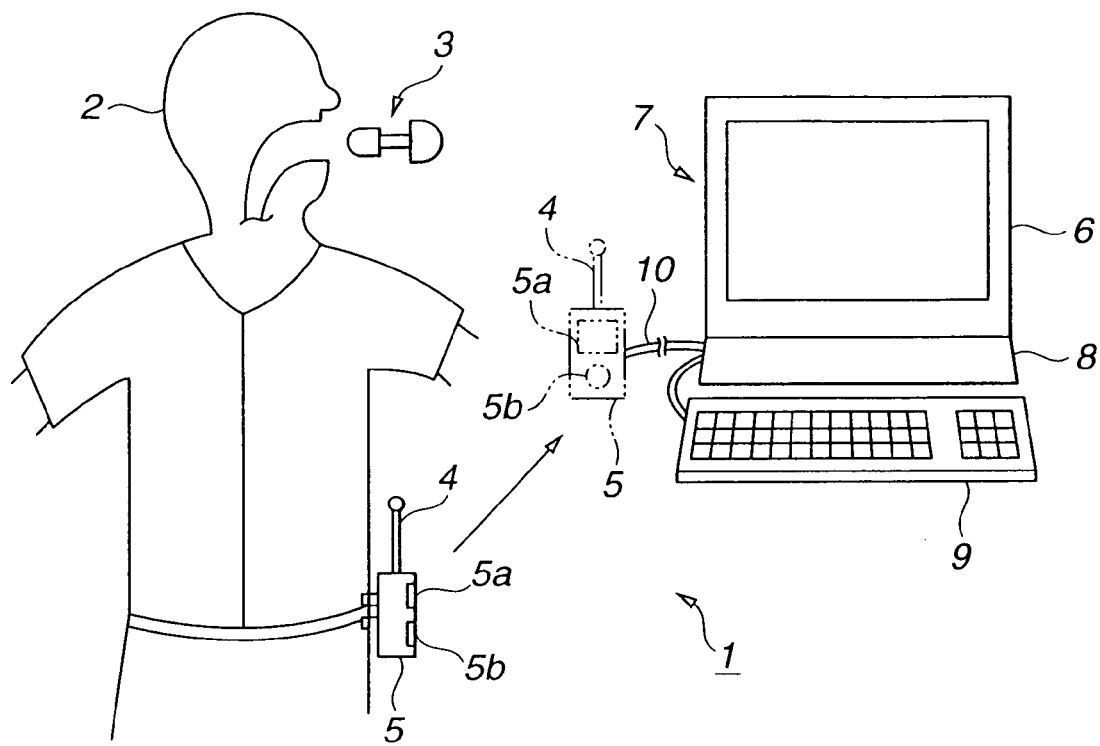
FIG. 1 illustrates the capsule-type endoscopic system of the first embodiment of the present invention.
Figure 2:
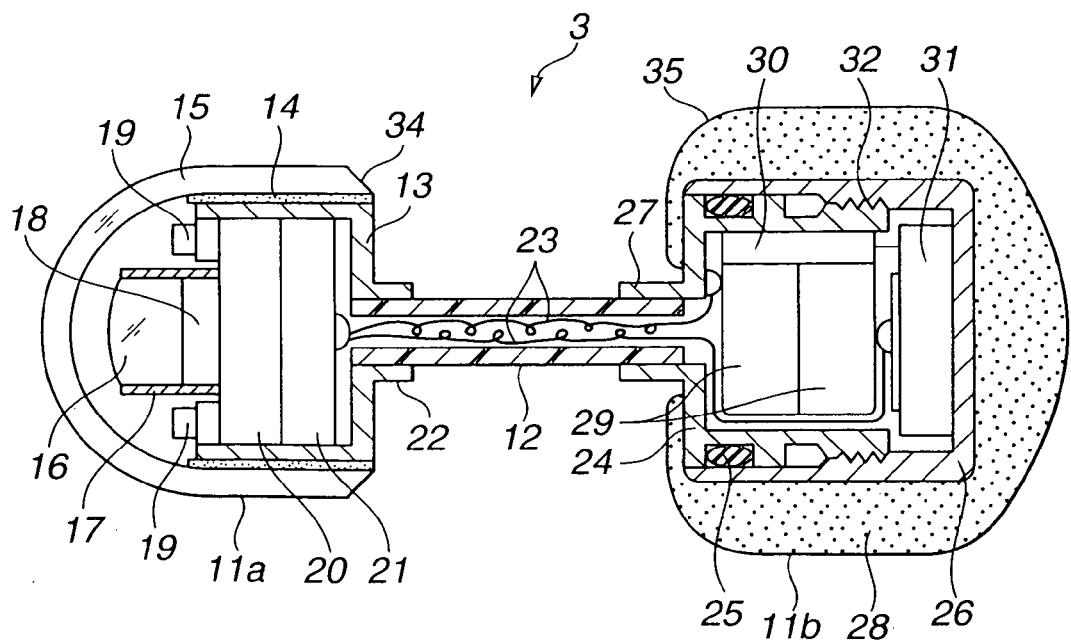
FIG. 2 is a sectional view illustrating the structure of the capsule-type endoscope of the first embodiment.
Figure 3:
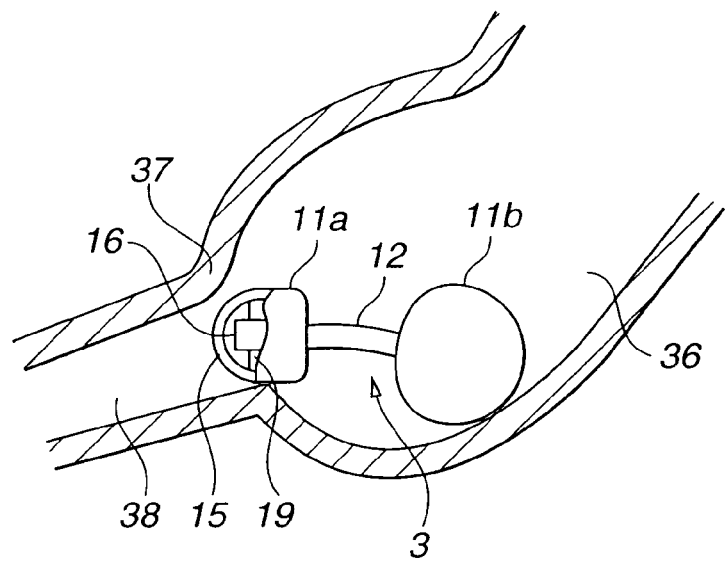
FIG. 3 illustrates the capsule-type endoscope of the first embodiment, which moves from the stomach into the duodenum.
Figure 4:
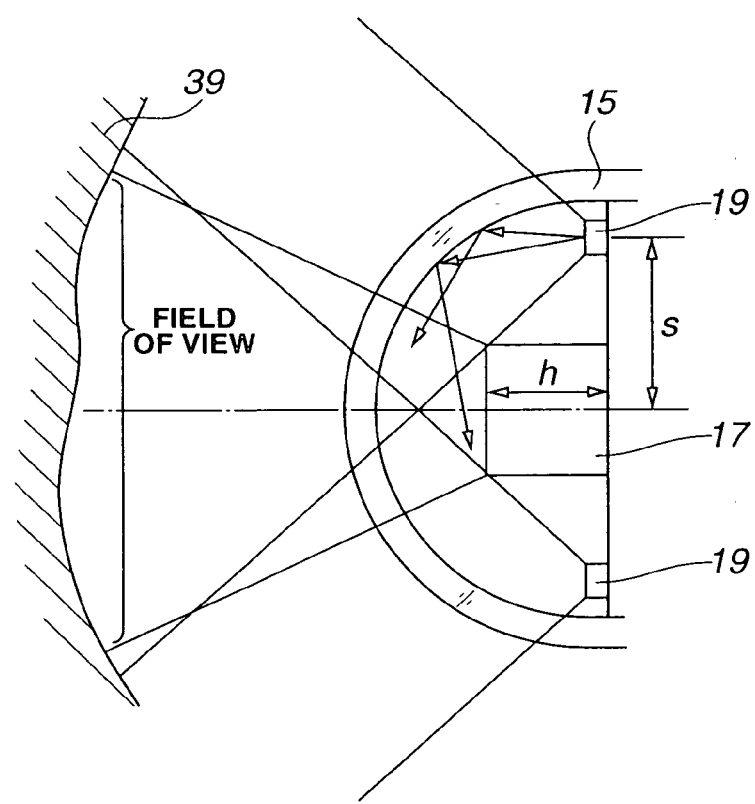
FIG. 4 illustrates the structure and functions of the illumination device and observation device component of the first embodiment.
Figure 5:
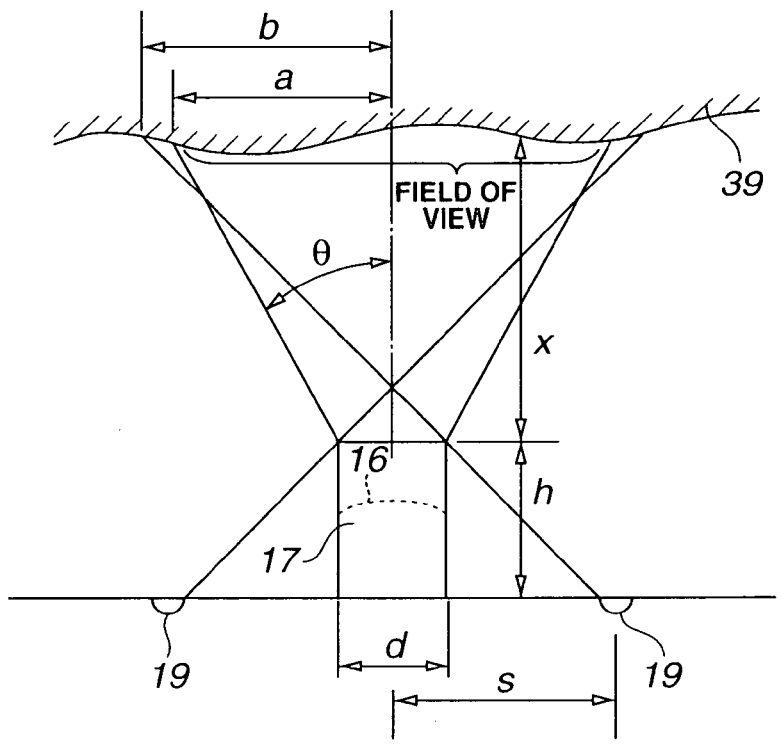
FIG. 5 illustrates a part of the structure shown in FIG. 4.
Figure 6:
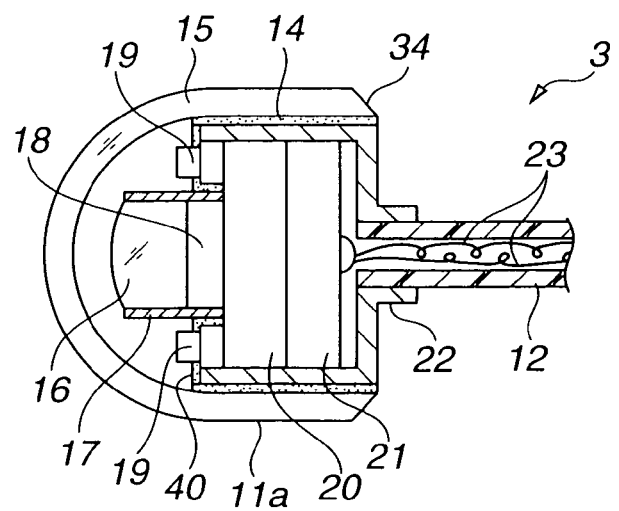
FIG. 6 is a sectional view illustrating the structure of a part of the capsule-type endoscope which is a modification example of the first embodiment.

FIGS. 1 to 6 illustrate the first embodiment of the present invention. FIG. 1 illustrates the structure of the capsule-type endoscopic system of the first embodiment. FIG. 2 illustrates the internal structure of the capsule-type endoscope of the first embodiment. FIG. 3 illustrate an example of utilization relating to the movement from the stomach to the duodenum. FIG. 4 illustrates the structure and functions of the illumination device and observation device components. FIG. 5 illustrates a part of the structure shown in FIG. 4. FIG. 6 illustrates the structure of a part of the capsule-type endoscope which is a modification example.

As shown in FIG. 1, a capsule-type endoscopic system 1 of the first embodiment of the capsule-type medical device of the present invention is composed of a capsule-type endoscope 3 of the first embodiment, which is swallowed by a patient 2 and used for examination inside the somatic cavities, an external unit 5 disposed outside the body of patient 2 and equipped with an antenna 4 for wireless reception of image information picked up by the capsule-type endoscope 3, and a personal computer (abbreviated as PC hereinbelow) 7 capable of taking in the images accumulated in the external unit 5 and displaying them on a monitor 6 by virtue of detachable connection of the external unit 5. The PC 7 is composed by connecting a keyboard 9 for data input and the monitor 6 to a PC body 8 and is detachably connected to the external unit 5 with an USB cable 10 or the like.

FIG. 2 illustrates the internal structure of the capsule-type endoscope 3 of the first embodiment.

The capsule-type endoscope 3 comprises a first capsule 11a and a second capsule 11b as two capsule-like hard units of different diameters and a soft flexible tube 12 connecting the capsules and having a diameter less than the diameter of the two capsules 11a, 11b, and has a structure in which the two capsules 11a, 11b are connected by the tube.

In the first capsule 11a, the cylindrical peripheral portion of a hard capsule frame 13 is water-tight sealed with a dome-like hard transparent cover 15 via a seal member 14, this cover also covering the opening of capsule frame 13. An image pickup device and an illumination device are housed inside the first capsule.

An objective lens 16 constituting the image pickup device (observation device) is mounted on a light-shielding lens frame 17 and disposed opposite the transparent cover 15 in the central portion of the internal space covered with the dome-like transparent cover 15. An image pickup element, for example, a CMOS image pickup device 18 is disposed in the image forming position of the objective lens.

Furthermore, for example, white LEDs 19 are disposed as illumination devices in a plurality of places around the lens frame 17, and the light emitted by the white LEDs 19 passes through the transparent cover 15 and illuminates the space outside thereof. Moreover, a drive circuit 20 for driving and inducing the emission of light by the white LEDs 19 and for driving the CMOS image pickup device 18, and a controller 21 for controlling this drive circuit 20 and provided with a function of conducting signal processing with respect to the output signals of CMOS image pickup device 18 are disposed on the rear surface side of CMOS image pickup device 18. The drive circuit and the controller are secured to the capsule frame 13.

Further, a connection socket 22 for connecting and securing one end of tube 12 is provided in the center of the end surface (back end surface) of capsule frame 13 on the side thereof opposite the transparent cover 15. One end of tube 12 is water-tightly connected and secured to the connection socket.

Moreover, one end of an electric cable 23 which is an electric connection member advanced the inside of the tube 12 is connected to the controller 21, and the other end thereof is connected to the second capsule 11b. The tube 12 is formed from a flexible tube made from polyurethane, poly(vinyl chloride), silicone, and the like.

The length of tube 12 linking the first capsule 11a and the second capsule 11b is almost equal to, or greater than the length of the smaller first capsule 11a.

The electric cable 23 is curled, laid in a zigzag manner, or spirally wound inside the tube 12 so that practically no tension is applied to the electric cable 23 even when the shape of tube 12 is changed.

In the second capsule 11b which is larger in size than the first capsule 11a, the open end side of capsule frame 24, which is a battery housing provided with a function of battery housing means, is detachably covered with a battery housing lid 26, for example, via a seal member 25 inserted in the cylindrical surface part thereof. The external part of the battery housing lid 26 is covered with an elastic resin cover 28, which serves as a protective cover, to a proximity of a connection socket 27 of tube 12 in the capsule frame 24. The elastic resin cover 28 can be put on or taken off by using an elastic force thereof.

A battery 29, for example, a button-type battery, a transmission-receiving, circuit 30, and an antenna 31 are enclosed in the capsule frame 24. The transmission-receiving circuit 30 is electrically connected to the controller 21, generates the signals which are to be transmitted, and demodulates the received signals. The antenna 31 is connected to the transmission-receiving circuit 30 and sends the image information picked up by the CMOS image pickup device 18 to the external unit 5 or receives control signals radio transmitted from the external unit 5.

The battery 29 serving as a power supply is connected so as to supply a drive power to the transmission-receiving circuit 29, controller 21, and drive circuit 20.

An external thread 32 is provided on the cylindrical side surface portion of the second capsule 11b, and an internal thread for engaging with the external thread 32 is provided on the inner peripheral surface of battery housing lid 26. Furthermore, a circular groove is provided on the cylindrical side surface portion of the second capsule 11b, and a seal member 25 for waterproofing, for example, such as an O-ring, is housed therein, thereby water-tightly sealing the inside of the capsule between the seal member and the battery housing lid 26 which is brought in contact therewith under pressure.

Furthermore, the other end of tube 12 is water-tightly secured, for example, with an adhesive to the connection socket 27 located in the central portion of capsule frame 24 on the side opposite the battery housing lid 26.

Moreover, the external unit 5 receives signals from the capsule-type endoscope 3 with the antenna 4, and the image demodulated by an internal signal processing circuit (not shown in the figure) is displayed on a liquid-crystal monitor 5a provided in the external unit 5 and also compressed and stored in the internal nonvolatile memory or a small hard disk or the like.

A control member 5b is provided in the external unit 5. By operating the control member 5b, it is possible to send a control signal in the form of electromagnetic wave from the antenna 4, and if the capsule-type endoscope 3 receives this control signal, the controller 21 can vary the illumination interval of illumination device and the image capturing period of the image pickup device.

For example, the capsule-type endoscope 3 usually conducts one cycle of illumination and image pickup within 2 seconds, but if control signals are once received with a short interval, one cycle of illumination and image pickup is conducted within 1 second. If the control signals with a short interval are received twice in a row, two cycles of illumination and image pickup are conducted within 1 second. Furthermore, if a cancel control signal is sent, the capsule-type endoscope 3 returns to the usual illumination and image pickup period.

Furthermore, connecting the external unit 5 to PC 7 upon completion of endoscopic examination with the capsule-type endoscope 3 makes it possible to load the image data accumulated by the external unit 5 into the PC 7 and to display them with the monitor 6.

In the capsule-type endoscope 3 of such a configuration, the two capsules 11a, 11b one of which is smaller than the other are linked by a flexible tube 12, and the image pickup device and illumination device are housed in the first capsule 11a. Furthermore, the battery 29 serving as a power supply and the antenna 31 are housed in the larger second capsule 11b, electric power is supplied to the image pickup device and illumination device via the electric cable 23 is passed through the inside of the tube 12, and the image signals picked up by the image pickup device are transmitted to the outside from the antenna 31.

In this case, making one of the capsules 11a, 11b smaller than the other facilitates swallowing and makes advancing easier. Furthermore, housing the illumination device and image pickup device on the front end side, namely on the end side opposite to the one connected with the tube 12, of the smaller first capsule 11a and illuminating zones ahead in the movement direction of capsule-type endoscope 3 allows to pick up images of the illuminated somatic cavities.

Furthermore, the rear side of the smaller first capsule 11a is corner cut and a chamfer 34 is provided so as to obtain an inclined or spherical surface. Thus, the periphery of the surface connected to the tube 12 which is a soft part linking the hard units is chamfered to obtain a spherical or inclined shape.

The outer periphery of the front portion of the larger second capsule 11b, which is connected by the tube 12, is also provided with a chamfer 35 to obtain an inclined or spherical shape improving the advancing ability. The chamfer 35 is made larger than the chamfer 34 on the back end side of the first capsule 11a to permit unobstructed passage.

Further, the electric cable 23 is made longer than the tube 12 to follow the deformation of flexible tube 12.

The length of tube 12 is equal to or greater than the length of the smaller first capsule 11a. Thus, providing a length exceeding the fixed value makes it easier to swallow the endoscope. When the length of tube 12 is within a range from the length almost equal to that of the smaller first capsule 11a to the length twice that, twisting or knotting of the soft linking unit is prevented.

In case of endoscopic examination of patient 2 who swallows the capsule-type endoscope 3 of the above-described embodiment, as shown in FIG. 1, making the two capsules 11a, 11b different in size allows them to be smoothly and easily swallowed, when the endoscope is swallowed with the smaller end forward, and also permits the movement direction to be controlled, as shown in FIG. 3.

As shown in FIG. 3, when the capsule-type endoscope 3 advances from a stomach 36, through a pylorus 37, to a duodenum 38, the smaller first capsule 11a easily enters first, thereby allowing the movement direction and observation direction to be matched.

The dome-like transparent cover 15 is provided on the front side of the smaller first capsule 11a so as to cover the front surface of this capsule, and this transparent cover 15 encloses the image pickup device and illumination device. The objective lens 16 constituting the image pickup device is fit into the light-shielding lens frame 17 for shielding the unnecessary light reflected from the inner side of the transparent cover 15 and protrudes forward beyond the illumination device. Thus, the light-shielding lens frame is provided around the observation device and the front surface of the light-shielding lens frame projects beyond the front surface of illumination device.

Because of its shape, the capsule-type endoscope 3 conducts illumination and observation (image pickup) through the dome-like window. In this case, the reflection and back reflection of the illuminated light on the inner surface of the dome-like transparent cover 15 provided on the front surface of illumination device and observation device can occur with a high probability and the observed image can contain a ghost component or flare. For this reason, the function of the light-shielding lens frame 17 is of major importance.

In the present embodiment, as shown in FIG. 4, when the height of lens frame 17 is represented by h and the distance between objective lens 16 and illuminating device is represented by s, the positional relationship of lens frame 17 and illumination device is set such as to prevent the light emitted from the illumination device and then reflected from the inner surface of transparent cover 15, as completely as possible, from entering the objective lens 16. In other words, the outer diameter and height of the light-shielding lens frame and the distance between the illumination device and observation device are set such as to substantially prevent the incidence of the unnecessary light such as the light emitted from the illumination device and then reflected from the inner surface of the dome-like observation window onto the observation device. For example, a part of the light emitted, as shown by the arrow, from one white LED 19 constituting the illumination device shown in FIG. 4 is reflected by the inner surface of transparent cover 15, but practically all the reflected light is prevented from entering the objective lens 16 located on the inner side of lens frame 17, thereby ensuring the field of view created by the objective lens 16.

Furthermore, the light that passed through the inner surface of transparent cover 15 and was reflected by the outer surface thereof is also prevented as completely as possible from entering the objective lens 16. As a result, random penetration of reflected light is substantially eliminated and observation performance is improved.

FIG. 5 is an expanded view of the main part of the structure shown in FIG. 4, which illustrates the effective illumination of the view field range.

As shown in FIG. 5, the range of field of view with respect to the observation object 39, which is defined by the objective lens 16 installed in the lens frame 17 disposed in the center, can be illuminated with white LEDs 19 serving as illumination devices and disposed on both sides of the range of field of view. Here, for the sake of simplicity, the objective optical system is represented by a combination of objective lens 16 and lens frame 17.

In the figure:
x: distance from the front surface of the objective optical system to the observation object 39,
h: height of objective optical system (from the end surface of the white LED 19),
d: diameter of the objective optical system,
θ: view angle of the objective optical system,
s: distance between the objective optical system and white LED 19,
a: radius of field of view,
b: illumination range.

As shown in FIG. 5, a and b are set such that a≦b. As a result, the range of field of view can be effectively illuminated, without shielding the illumination light with the objective optical system.

Here, $$a = d/2 + x \tan \theta$$

$$b = (x/h) \cdot (s - d/s) - d/2.$$

The operation of the present embodiment will be described below.

When somatic cavities of the patient 2 are examined with the capsule-type endoscope 3, the battery 29 has to be housed as shown in FIG. 2. In this case, the portion where the battery 29 is housed can be detached by unscrewing. If the elastic resin cover 28 is removed and the battery housing lid 26 is removed by unscrewing, then a new battery 29 can be housed in an easy manner.

When the capsule-type endoscope 3 is to be used, the patient 2 or doctor installs the battery 29 and screws the battery housing lid 26 into the capsule frame 24, which is one part of the split battery housing unit, that is, assembles the battery housing unit, thereby turning the power supply ON and initiating the capturing of images or transmission and receiving of signals. The power supply can be thus turned ON in an easy manner, and no special switch is required. Conversely, when the capsule-type medical device is discarded, the battery can be easily removed, which is beneficial for the environment.

Further, in the present embodiment, the battery 29 is placed in the second capsule 11b. Therefore, if it is broken, problems can be associated with electric discharge or leakage. To prevent the breakage, the capsule is protected with the elastic resin cover 28. Further, water-tight sealing with the seal member 25 such as an O-ring is implemented to prevent water and other body fluids from penetrating into the space where the battery 29 is housed.

As shown in FIG. 1, the patient 2 can smoothly swallow the medical capsule 3 by inserting it into the mouth the first capsule 11a side first, this first capsule having a small outer diameter.

The capsule-type endoscope 3 conducts illumination and image pickup with a constant cycle, and the picked-up image information is wireless transmitted from the antenna 31. The image information is received by the external unit 5 and displayed on the liquid-crystal monitor 5a or stored.

Therefore, the endoscopic examination crew can monitor the information with the liquid-crystal monitor 5a. Further, since the outer diameter of the first capsule 11a is less than that of the second capsule 11b and the first capsule 11a advances easier than the second capsule 11b, the first capsule 11a readily becomes ahead in the movement direction. In other words, when the endoscope advances from the stomach 36, through the pylorus 37, to the duodenum 38, as shown in FIG. 3, it easily advances to the deep zones smaller first capsule 11a first.

Furthermore, in this case since the illumination and image pickup devices are provided on the distal end of the first capsule 11a, the image of somatic cavities in the movement direction can be picked up and images, which can be easily diagnosed in the same manner as diagnostic images obtained with the usual endoscope, can be also obtained.

In another modification example, the below-described image pickup device may be used instead of the CMOS image pickup device.

The image pickup device used herein employs a threshold voltage modulation image sensor (VMIS), which is the next-generation image sensor, possessing the merits of both the above-described CMOS image pickup device and the CCD (charge coupled device). The structure of this sensor is entirely different from that of the conventional CMOS sensor in which the light receiving unit is composed of 3-5 transistors and photodiodes. Thus, the VMIS has a structure employing a technology of modulating the threshold value of a MOS transistor with a charge generated by the received light and outputting the changes of the threshold value as the image signals.

Such an image sensor features a combination of high quality of CCD and a high degree of integration and low power consumption of CMOS sensor.

For this reason, it was employed in the disposable capsule-type endoscopes. Using such a feature makes it possible to realize a disposable endoscope (soft or hard) or a low-price endoscope. The voltage modulation image sensor (VMIS) can be used not only in such endoscopes, but also in usual videoscopes. In addition, such voltage modulation image sensor (VMIS) has the below-described excellent features.

The structure is simple, with one transistor per one image sensor.

The VMIS has excellent photoelectric characteristic such as high sensitivity and high dynamic range.

Since the sensor can be fabricated by a CMOS process, a high degree of integration and low cost can be realized.

There are sensors of a variety of types, such as QCIF (QSIF) size, CIF (SIF) size, VGA type, SVGA type, XGA type, and the like. In the capsule-type endoscope with wireless communication of the present invention, small sensors of "QCIF (QSIF) size" and "CIF (SIF) size" are especially preferred from the standpoint of wireless transmission speed, power consumption, and because they are easy to swallow.

FIG. 6 illustrates a modification example of the first embodiment and shows part of the first capsule 11a of this modification example.

In this modification example, a water-tight seal 40 is additionally implemented in white LEDs 19, objective lens 16, and lens frame 17 located inside the transparent cover 15 in the first capsule 11a shown in FIG. 2. In other words, a structure is employed in which the illumination device and observation device ensure water tightness for the hard unit with no dome-like observation window attached. Thus, the transparent cover 15 has a water-tight structure inside thereof on the front side, but even when cracks appear in the transparent cover 15 and it loses the waterproofing function thereof, using the water-tight seal 40 provides a water-tight structure for the entire surface facing the transparent cover 15 inside the transparent cover 15 so as to ensure electric insulation preventing the permeation of water into the electric system, such as the internal drive circuit 20. The side surface portion is sealed with the seal member 14 in the same manner as shown in FIG. 2.

With such a structure no water permeates into the electric system located inside the transparent cover 15 and electric insulation properties can be maintained even when cracks appear in the cover and it loses the waterproofing function thereof.

The present embodiment has the following effects.

Swallowing is facilitated by splitting one capsule in two to decrease the size thereof and making one of the resulting capsules less than the other. In other words, easiness of swallowing can be improved. Furthermore, changing the size of the capsules readily matches the movement direction with the observation direction. In other words, the observation ability can be improved.

Further, adjusting the arrangement of the objective optical system and also the illumination and transparent cover 15 reduces random penetration of reflected light. In other words, the observation ability can be improved.

Moreover, the power supply ON/OFF and battery replacement can be conducted in an easy manner. The endoscope is easy to handle and environment-friendly.

Since waterproofing of inner circuits is maintained even when cracks appear in the transparent cover, accidents are prevented.

In another modification example of the present embodiment, the front surface of the objective lens 16 of the lens frame 17 may be brought in contact with the inner surface of the transparent cover 15. In this case, the transparent cover 15 has high resistance to deformation even when a large external force is applied thereto.

In other words, since the objective lens 16 or lens frame 17 is arranged so as to be in contact with the transparent cover 15, the transparent cover 15 is not deformable nor rupturable and, therefore, the strength can be increased.

Second Embodiment

The second embodiment of the present invention will be described hereinbelow with reference to FIGS. 7 to 10.

Figure 7:
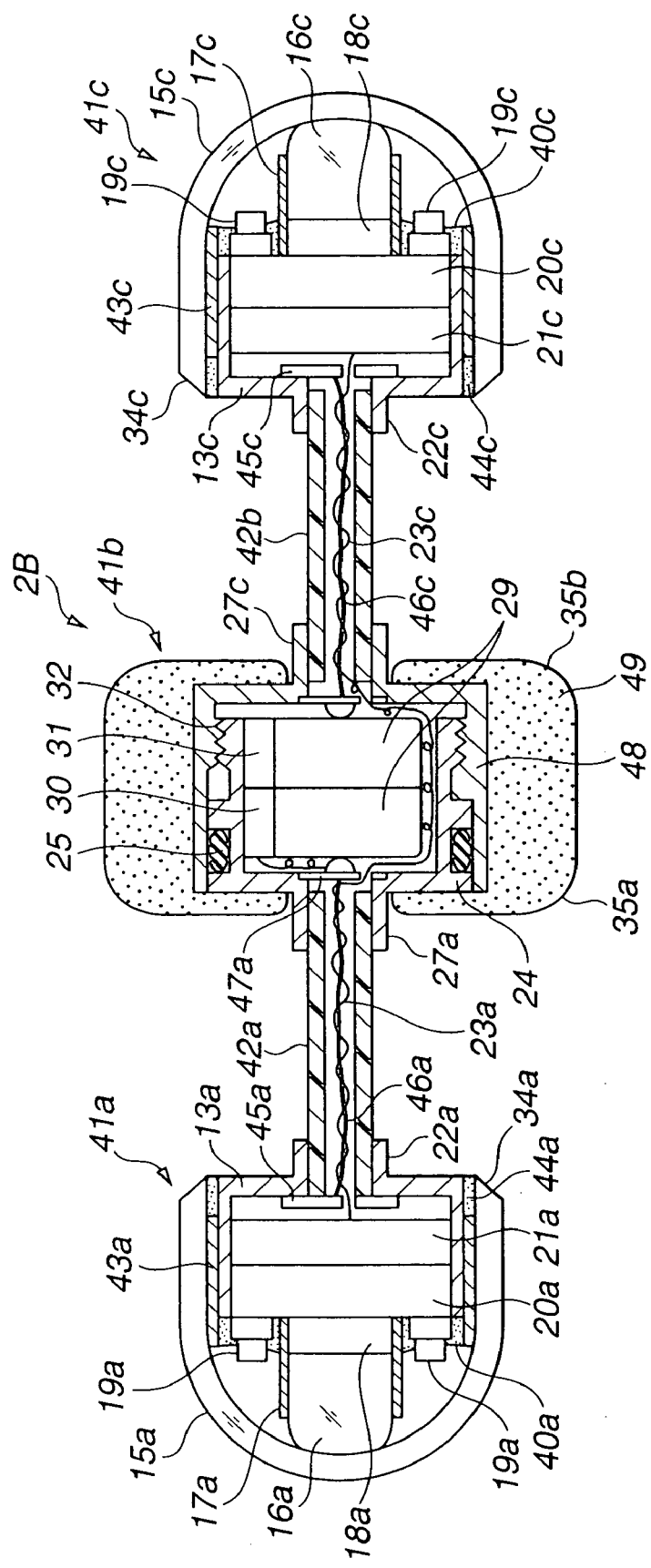
FIG. 7 is a sectional view illustrating the structure of the capsule-type endoscope of the second embodiment of the present invention.

FIG. 7 is a sectional view illustrating a capsule-type endoscope 2B of the second embodiment of the present invention. This capsule-type endoscope 2B comprises three capsules 41a, 41b, 41c and flexible tubes 42a and 42b linking the adjacent capsules 41a, 41b and the adjacent capsules 41b, 41c.

In this case, the first capsule 41a and third capsule 41c disposed on both ends have almost the same outer diameter, whereas the second capsule 41b disposed in the center with respect thereto has a larger outer diameter.

Furthermore, the first capsule 41a and third capsule 41c have a structure similar to that of the first capsule 11a of the first embodiment, and the second capsule 41b has a structure similar to that of the second capsule 11b.

In the first capsule 41a, a cylindrical permanent magnet 43a is provided to surround the cylindrical peripheral portion of a capsule frame 13a and the opening of capsule frame 13a is covered with a dome-like transparent cover 15a. The circumferential part of this opening is water-tightly fixed with a waterproofing adhesive 44a, and an image pickup device and an illumination device are housed inside thereof. A ferroelectric substance producing a strong magnetic force may be used instead of the permanent magnet 43a.

An objective lens 16a constituting the image pickup device (observation device) is mounted on a light-shielding lens frame 17a and disposed opposite the transparent cover 15a in the central portion of the internal space covered with the dome-like transparent cover 15a. An image pickup element, for example, a CMOS image pickup device 18a is disposed in the image forming position of the objective lens. For example, the objective lens 16a is disposed so that the outer surface thereof is in contact with the inner surface of transparent cover 15a.

Furthermore, for example, white LEDs 19a are disposed as illumination devices in a plurality of places around the lens frame 17a, and the light emitted by the white LED 19a passes through the transparent cover 15a and illuminates the space outside thereof.

Moreover, a drive circuit 20a for driving and inducing the emission of light by the white LEDs 19a and for driving the CMOS image pickup device 18a, and a controller 21a for controlling this drive circuit 20a and provided with a function of conducting signal processing with respect to the output signals of CMOS image pickup device 18a are disposed on the rear surface side of CMOS image pickup device 18a. The drive circuit and the controller are secured to the capsule frame 13a.

As shown in FIG. 6, a water-tight seal 40a is implemented on the inner side of the transparent cover 15a, and the electric system such as the drive circuit 20a and the like can be maintained in an electrically insulated state by the water-tight seal 40a even when cracks appear in the transparent cover 15a and water tightness provided by the portions covered with the transparent cover 15a is lost.

Further, a connection socket 22a for connecting and securing one end of a tube 42a is provided in the center of the end surface of capsule frame 13a on the side thereof opposite the transparent cover 15a. One end of the tube 42a is water-tightly connected and secured to the connection socket.

Moreover, one end of an electric cable 23a which is passed through the inside of the tube 42a via the opening of a disk-like latch 45a is connected to the controller 21a, and the other end thereof is connected to the second capsule 41b.

The latch 45a is connected to a latch 47a of the second capsule 41b via a linking metallic wire 46a inserted into the tube 42a and provides free bendability for the flexible tube 42a, so as to prevent disrupting the linkage between capsules 41a and 41b.

An electric cable 23a is, for example, wound around the linking metallic wire 46a and inserted into the tube 42a. A chamfer 34a is formed on the rear peripheral portion of the first capsule 41a by cutting it at an angle or corner cutting so as to obtain a spherical shape.

The third capsule 41c has a similar structure. The components assigned with the reference symbol (a) that were explained in describing the first capsule 41a are now assigned with the reference symbol (c) and the explanation thereof is omitted.

In the second capsule 41b which is larger in size than the first and third capsules 41a, 41c, a seal member 25 is inserted, for example, into the cylindrical side surface of a capsule frame 24 serving as battery housing means and the end side thereof which is opened toward the third capsule 41c is detachably covered with a battery housing lid 48.

Connection sockets 27a, 27c for connecting and securing the tubes 42a, 42b are provided in the center of respective end surfaces of the capsule frame 24 and the battery housing lid 48, and the tubes 42a, 42b are water-tightly connected and fixed, for example, with a waterproofing adhesive.

Further, the outer peripheral portions of the batteries housing the lid 48 and the capsule frame 24 are covered with an elastic resin cover 49 up to the vicinity of connection sockets 27a, 27c.

The capsule frame 24 encloses, for example, a button-type battery 29, a transmission-receiving circuit 30, and an antenna 31. The transmission-receiving circuit 30 is electrically connected to controllers 21a, 21c, generates signals to be transmitted, and demodulates the received signals. The antenna 31 is connected to the transmission-receiving circuit 30 and sends the image information captured by the CMOS image pickup devices 18a, 18c to the external unit (not shown in the figure) or receives control signals wireless transmitted from the external unit.

The battery 29 is connected so as to supply drive electric power to the transmission-receiving circuit 30, controllers 21a, 21c, and drive circuits 20a, 20c.

An external thread 32 is provided on the cylindrical side surface of the second capsule 41b, and an internal thread, which is to be engaged with the external thread 32, is provided on the inner peripheral surface of the battery housing lid 48. Further, a circumferential groove is provided on the cylindrical side surface of the second capsule 41b and a seal member 25 such as an O-ring is housed therein, thereby water-tightly sealing the inside of the capsule between the seal member and the battery housing lid 48 which is brought in contact therewith under pressure.

In the capsule-type endoscope 2B of such a structure, three capsules 41a, 41b, 41c obtained by splitting into three portions are linked by the flexible tubes 42a, 42b. In this case, both end capsules 41a, 41c are of almost the same size, and the central capsule 41b is larger than the two end capsules 41a, 41c.

The two end capsules 41a, 41c are provided with an illumination device, image pickup device, drive circuits used for illumination and image pickup devices, and a processing circuit for the image pickup device. The central capsule 41b is provided with the battery 29, transmission-receiving circuit 30, and antenna 31, and various functions of the two end capsules 41a, 41c commonly use the battery 29 and transmission-receiving circuit 30 of the central capsule.

Further, exchange of electric power and signals between the three capsules 41a, 41b, 41c is conducted by electric cables 23a, 23c located inside the flexible tubes 42a, 42b. Linking metal wires 46a, 46b are passed through the inside of the tubes 42a, 42b so that the tubes 42a, 42b can be freely bent without disrupting the connection of capsules 41a, 41b and 41b, 41c.

Further, chamfers 35a, 35b larger than the above-described chamfers 34a, 34c are formed in the elastic resin cover 49, which serves as a protective cover, in the corner portion facing the first capsule 41a and the corner portion facing the third capsule 41c, respectively.

The operation of this embodiment will be described below.

Figure 8:
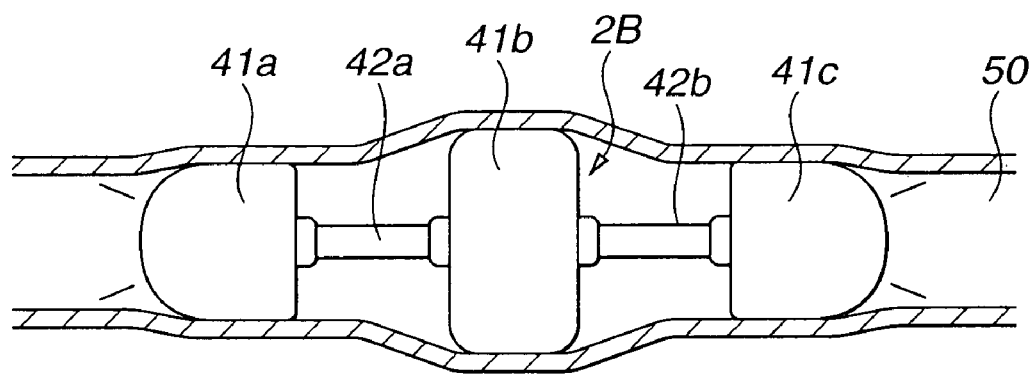
FIG. 8 illustrates the state of examining the inside of a somatic cavity with the capsule-type endoscope of the second embodiment.

Since the size of the two end capsules 41a, 41c is smaller than that of the central capsule 41b, any of the two end capsules moves first in a somatic cavity 50, as shown in FIG. 8. Therefore, zones ahead and behind in the movement direction can be observed with the two end capsules 41a, 41c, each being provided with the illumination and image pickup devices. When the endoscope moves leftward, as shown in FIG. 8, the capsule 41a illuminates the zone ahead and picks up the images therefrom, and the capsule 41c illuminates the zone behind and picks up the images therefrom. The reverse is the case when the endoscope moves rightward.

Figure 9:
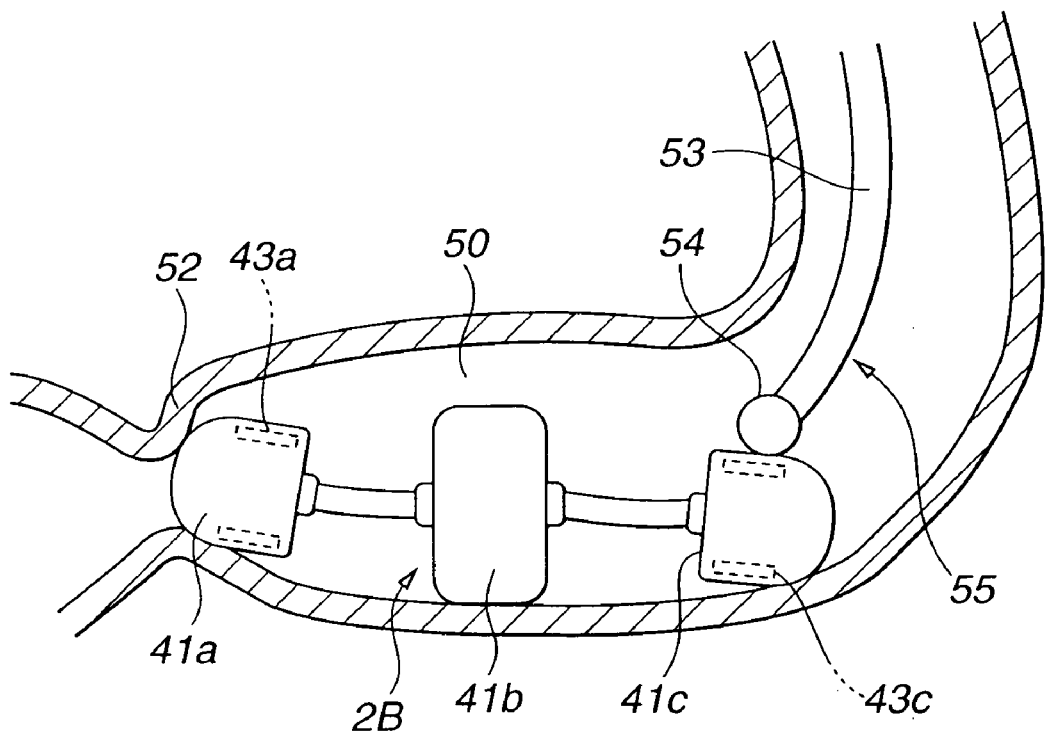
FIG. 9 illustrates the state of recovering the endoscope with a recovery tool when the endoscope is blocked in an isthmus.

In the present embodiment, cylindrical permanent magnets 43a, 43c or magnetic substance is provided in both end capsules 41*a*, 41*c*. As shown in FIG. 9, the permanent magnets 43*a*, 43*c* or magnetic substance makes it possible to recover the endoscope easily with a recovery tool 55 provided with a permanent magnet 54 at a front end of a cord-like member 53 when the capsule-type endoscope 2B is stuck and cannot advance through an isthmus 51 in the somatic cavity 50 and has to be recovered.

In other words, when the front end of the recovery tool 55 is brought close to the capsule-type endoscope 2B, the permanent magnet 54 is attracted to the permanent magnet 43*a* or 43*c* due to a magnetic force acting between the permanent magnet 54 at the front end of recovery tool 55 and the permanent magnet 43*a* or 43*c* at the capsule-type endoscope 2B. The capsule-type endoscope 2B can be then easily pulled out, that is, recovered by pulling out the recovery tool 55.

The above explanation is related to the recovery operation, but the permanent magnets 43*a*, 43*c* or magnetic substance can be also used for remotely controlling the position or orientation of the capsule-type endoscope 2B inside a somatic cavity by an external magnetic field.

The effect of the present embodiment will be described below.

Of the three above-described hard units, the outer diameter or length of the two end hard units is smaller than that of the hard unit other than the two end units. In particular, splitting a capsule in three decreases the size of capsule body and makes it easy to swallow the capsule. Thus, easiness of swallowing can be improved. In this case, swallowing can be made even more easier by decreasing the size of the capsules 41*a*, 41*c* located on both sides of central capsule 41*b*. The outer diameters or lengths of the two end hard units are almost the same.

Since the illumination devices and image pickup devices are provided in capsules 41*a*, 41*c* at the both sides, the observation direction can be the same as the movement direction and zones ahead and behind in the movement direction can be observed at the same time. Therefore, observation performance is improved. Further, since the size of capsules 41*a*, 41*c* located on both sides of the central capsule 41*b* is decreased, movement is facilitated.

Further, since the power supply function and signal transmission and receiving function are made common for a plurality of illumination devices and image pickup devices, the number of components can be decreased, which is beneficial for size reduction. In other words, size can be reduced and easiness of swallowing can be improved. The function of control unit may be also made common.

Further, providing the cylindrical permanent bodies 43*a*, 43*c* or magnetic substance allows the recovery or magnetic guidance. The recovery is facilitated and operability is improved.

Figure 10:
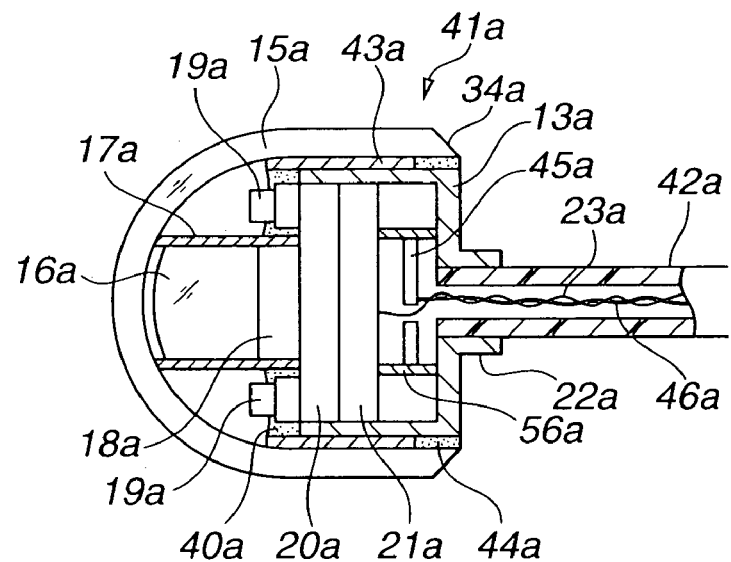
FIG. 10 is a sectional view illustrating the first capsule portion in the modification example of the second embodiment.

FIG. 10 illustrates a part of the first capsule 41*a* as a modification example of the present embodiment.

One end of a linking metal wire 46*a* located inside the tube 42*a* connecting the capsules 41*a*, 41*b*, on the side of capsule 41*a*, as shown in FIG. 10, has a slidable latch structure.

Thus, a latch 45*a* located inside the capsule 41*a* is disposed so that it is free to slide forward and backward inside a tubular body (ring) 56*a* disposed between the rear surface of controller 21*a* and the inner surface of capsule frame 13*a*.

Further, in the present embodiment, a lens frame 17*a* is abutted with the inner surface of the transparent cover 15*a*.

The resulting effect is that the transparent cover 15*a* is reinforced and the resistance thereof to external forces is improved.

Further, in the present embodiment, the linking metal wires 46*a*, 46*c* located inside the tubes 42*a*, 42*c* connecting the three capsules were separate from electric cables 23*a*, 23*c*, but in a structure of yet another modification example, the electric cables 23*a*, 23*c* may also serve as the linking metal wires 46*a*, 46*c*.

The resulting effect is that the structure can be simplified.

A structure may be also used in which one end of the linking metal wire is made slidable, as shown in FIG. 10, and the electric cables 23*a*, 23*c* also serve as the linking metal wires 46*a*, 46*c*. In this case, a sliding latch 45*a* may be provided with an electric contact and electrically connected to the controller 21*a* via the tubular body 56*a*.

In yet another modification example, a VMIS may be used instated of the CMOS image pickup device.

Third Embodiment

Figure 11:
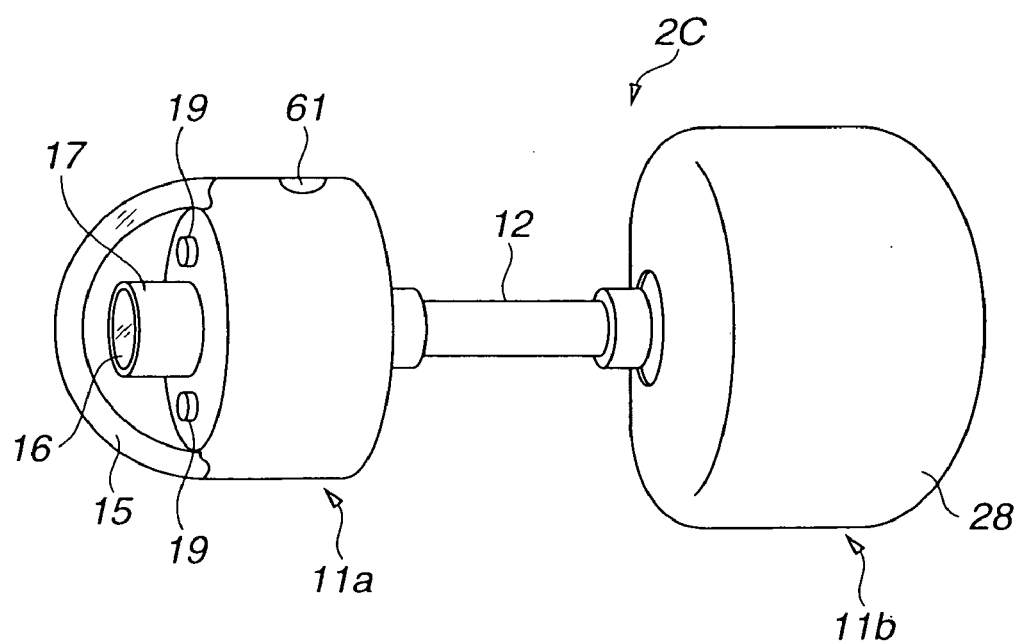
FIG. 11 is a perspective view, with a partial cut-out, of the structure of the capsule-type medical device of the third embodiment of the present invention.

The third embodiment of the present invention will be described below with reference to FIGS. 11 to 13. FIG. 11 illustrates a capsule-type medical device 2C which is the third embodiment of the present invention. Structural components identical to those of the first embodiment are assigned with the same reference symbols and the explanation thereof is omitted.

The capsule-type medical device 2C has a structure in which a variety of sensor means 61 such as a pH sensor, optical sensor, temperature sensor, pressure sensor, blood sensor (hemoglobin sensor), and the like are provided, for example, as in the first capsule 11*a*, for example, in the capsule-type endoscope 2 of the first embodiment.

Various sensor means 61 are secured to the outer member of the capsule, such as the transparent cover 15, so that sensing zone of sensor means 61 is exposed to the outside and the inside of the capsule is maintained in a water-tight state. Otherwise, the structure is the same as in the first embodiment.

Data such as chemical parameters (pH value) of body fluids, brightness inside a somatic cavity, temperature of various organs, pressure applied by the inner surface of somatic cavities to the outer surface of the capsule when the capsule advances therethrough, amount of hemoglobin in various organs (presence of hemorrhage) are obtained from the sensing zones. The data obtained are temporarily accumulated in a memory (not shown in the figures) located inside the capsule and then transmitted by the transmission-receiving circuit 30 and antenna 31 to a receiver such as the external unit 5 located outside the body. By comparing the data obtained by the receiver with the standard values, the medical crew, such a doctor or nurse, can externally establish the presence of abnormalities, such as disease or hemorrhage, and to determine the capsule advancing position or state.

In particular, diagnostics of gastroenterological diseases or physiological analysis can be conducted with high efficiency by painlessly establishing the pH value of hemoglobin level in digestive organs of the living body with the capsule-type medical device 2C. Highly efficient examination can be conducted by providing a plurality of sensors according to the object of examination.

Figure 12:
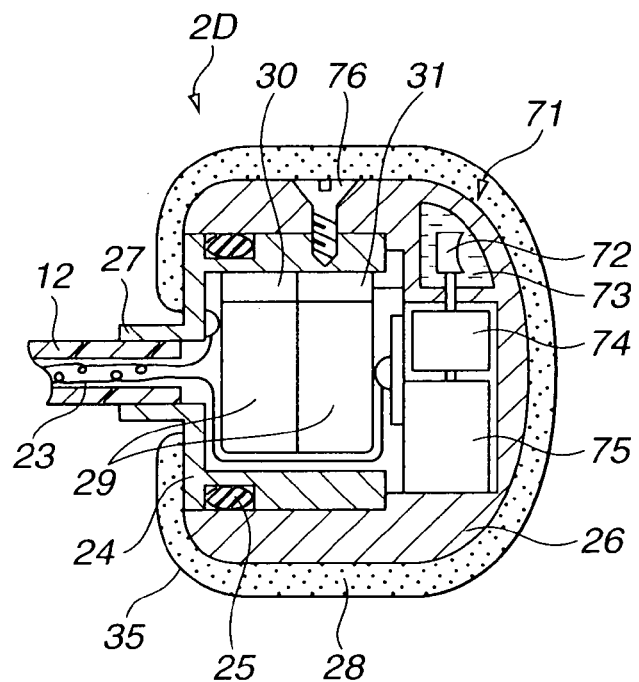
FIG. 12 is a sectional view illustrating the configuration of the main components of the capsule-type medical device of the first modification example of the third embodiment of the present invention.

FIG. 12 illustrates a part of the capsule-type medical device 2D which is a modification example of the third embodiment. In the present embodiment, an ultrasound probe 71 is additionally provided in the second capsule 11*b* of the first embodiment. In this case, for example, a battery housing lid 26 is formed with a material transmitting ultrasound waves, a sealed space is formed in the battery housing lid 26, a rotary-type ultrasound oscillator 72 is housed inside this space, and the area around the oscillator is filled with a transfer medium 73.

The ultrasound oscillator 72 is rotated by a motor 74. The elastic resin cover 28 of the external surface of the capsule around the ultrasound oscillator 72 functions as an acoustic lens of ultrasound oscillator 72. The battery housing lid 26 is detachably secured to a capsule frame 24 with a screw 76.

The ultrasound oscillator 72 makes possible the ultrasound tomography inside the somatic cavities, driving and signal processing being conducted by the control circuit 75. Data obtained are transmitted to the external receiver in the same manner as described above. As a result, diagnostics of the presence of abnormalities in the depth direction of deep portions of somatic cavities such as a small intestine can be conducted. If a structure is used with observation devices on both sides, then diagnostics of both the surface and deep portions in somatic cavities can be conducted. An ultrasound probe with an electronic scanning system rather than mechanical scanning system may be also used.

Figure 13:
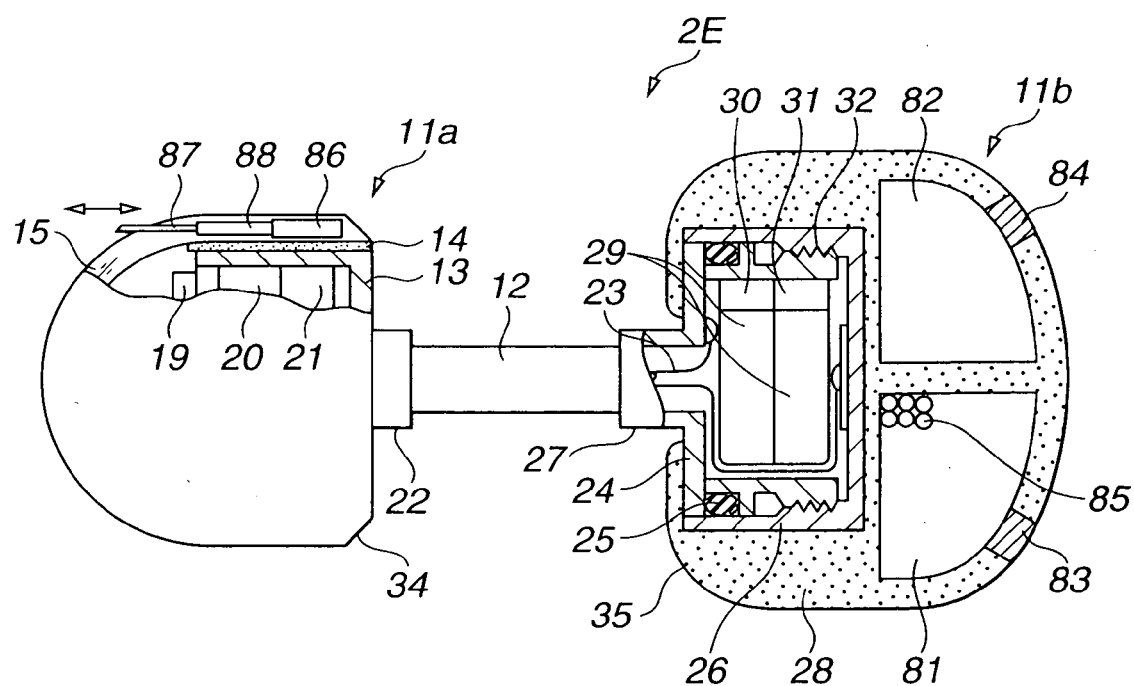
FIG. 13 illustrates the configuration of the main components of the capsule-type medical device of the second modification example of the third embodiment of the present invention.

FIG. 13 illustrates a capsule-type medical device 2E of the second modification example. This capsule-type medical device 2E is provided with treatment-therapy means.

In the capsule-type medical device 2E, a medicine compartment 81 and a body fluid compartment 82 are provided, for example, in the elastic resin cover 28 in the second capsule 11b, for example, in the capsule-type endoscope 2 of the first embodiment.

The medicine compartment 81 and body fluid compartment 82 have openings that are open on the outer surface of the capsule, and the openings are covered with soluble membranes 83, 84 composed of fatty acid membranes or the like that are digested by the liquid present in intestines or of gelatin consumed by gastric juice. A medicine 85 for treatment is enclosed in the medicine compartment 81. Once the capsule-type medical device 2E has arrived to the target location, the soluble membrane 83 is dissolved, the opening is opened, and the medicine 85 is directly administered. At the same time, body fluid can be sucked into the body fluid compartment 82.

Further, a linear actuator 88 for driving a syringe 87 so that it can be protruded is provided, for example, inside a part of transparent cover 15 in the first capsule 11a, this syringe having a compartment 86 accommodating a hemostatic drug.

Thus, once a hemorrhaging zone has been established by a blood sensor or observation device, usually a procedure can be employed by which the syringe 87 for injecting the hemostatic drug accommodated inside the capsule is projected in response to a signal from the external unit 5 located outside the body and a powdered drug or ethanol which is the hemostatic drug located inside the compartment 86 is sprayed over the hemorrhaging zone to stop bleeding.

Embodiments composed by partially combining the above-described embodiments are also covered by the present invention.

As described above, in accordance with the present invention, a capsule-type medical device which is advanced the inside of the somatic cavities and lumens of human being or animals for conducting examination, therapy, or treatment comprises at least two hard units and a soft linking unit which links the aforesaid plurality of the hard units and has a diameter less than that of any of the hard units, wherein one of the plurality of hard units is different in size from other hard units. Therefore, when the smaller hard unit is swallowed first, the medical device can be easily swallowed and the smaller unit can easily be advanced the inside of the lumens.

Fourth Embodiment

Figure 14:
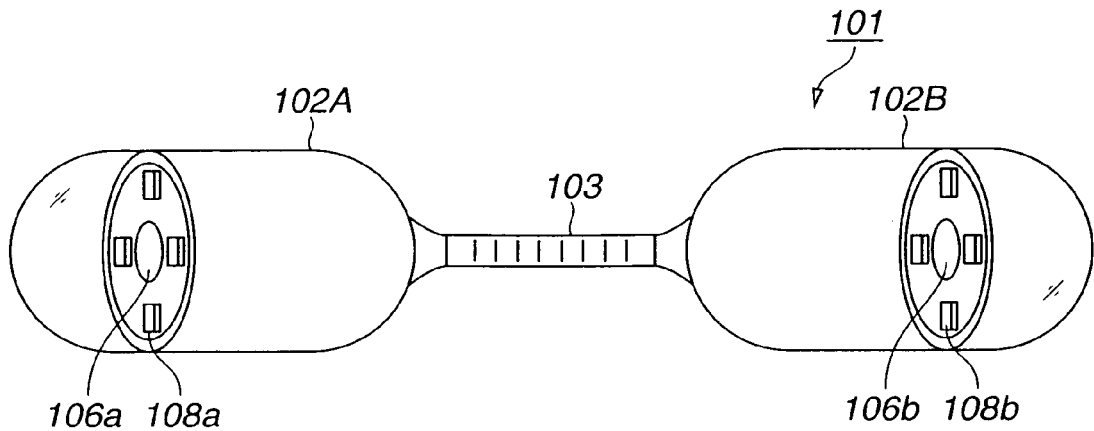
FIG. 14 illustrates the external appearance of the capsule-type endoscope of the fourth embodiment of the present invention.
Figure 15:
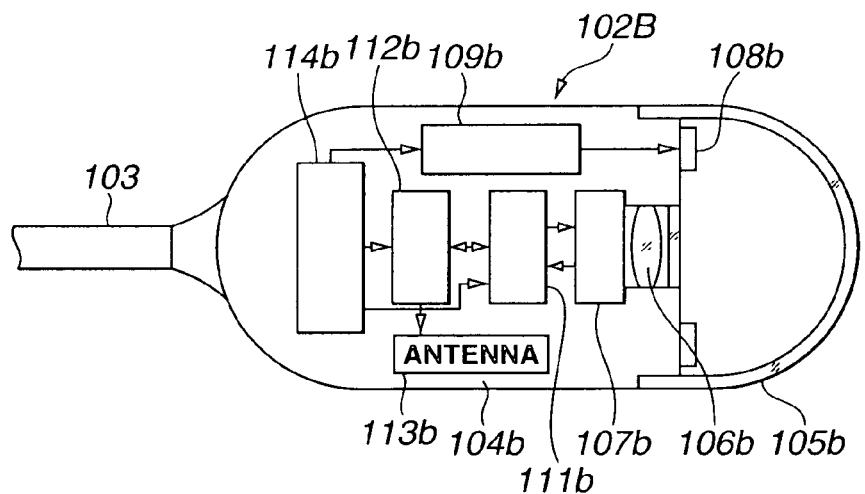
FIG. 15 illustrates the internal structure of one capsule body of the fourth embodiment of the present invention.
Figure 16A:
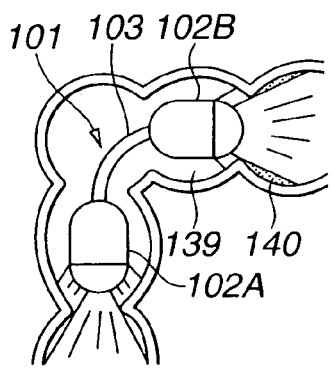
FIG. 16A and FIG. 16B explain the operation in the usage state of the capsule-type endoscope of the fourth embodiment.
Figure 16B:
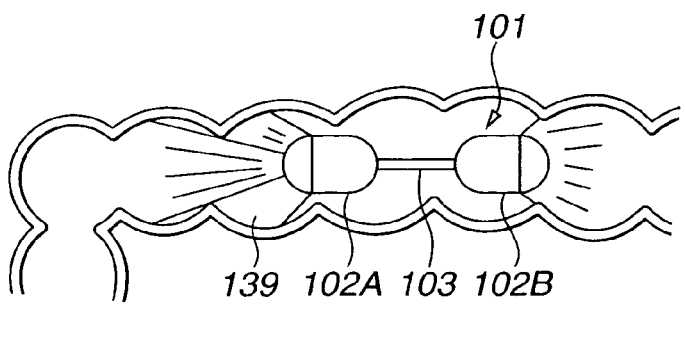
Figure 17A:
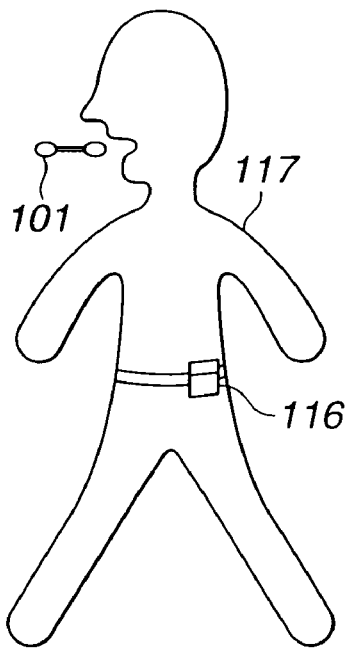
FIGS. 17A to 17D illustrate the sequence of operations in conducting the endoscopic examination according to the fourth embodiment.
Figure 17B:
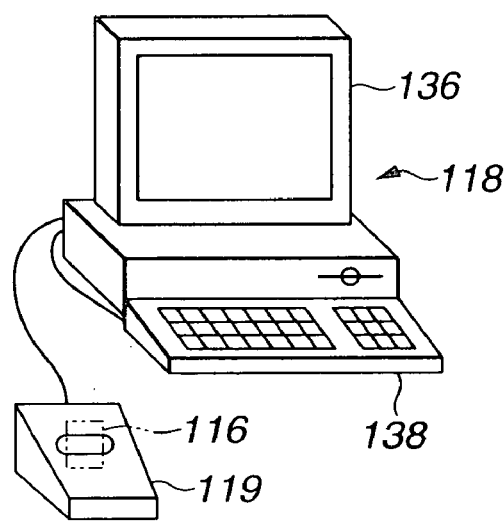
Figure 17D:
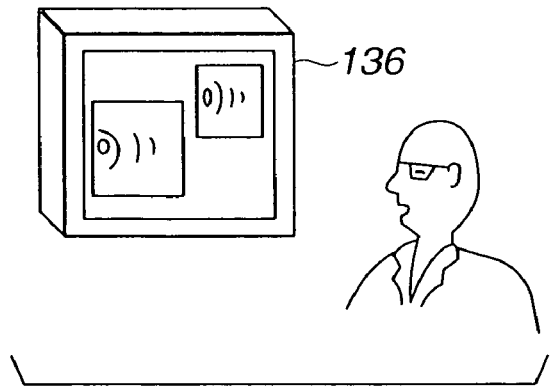
Figure 17C:
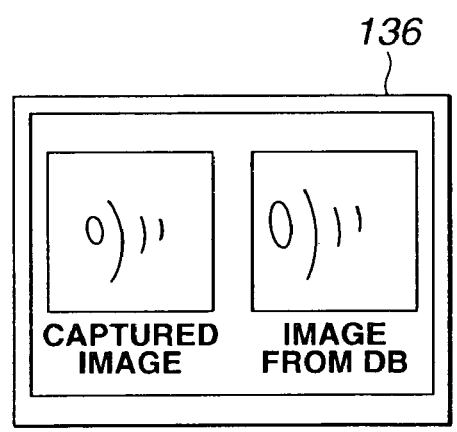
Figure 18:
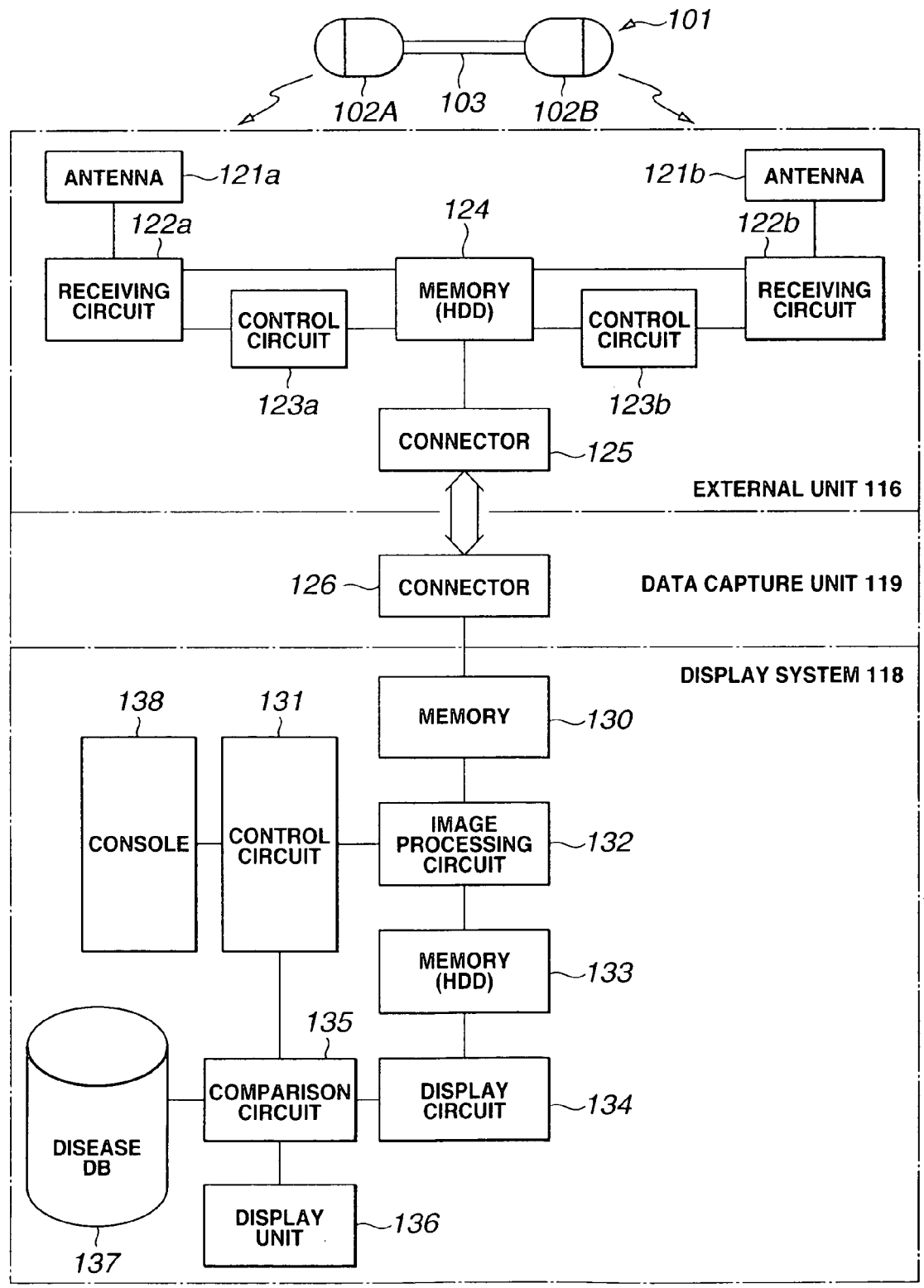
FIG. 18 is a block-diagram illustrating the configuration of the electric system of the external unit and display system of the fourth embodiment.
Figure 21:
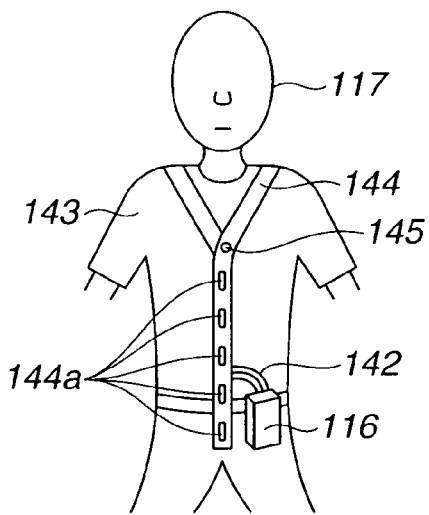
FIG. 21 illustrates a modification example of the antenna configuration of the fourth embodiment.

FIGS. 14 to 21 illustrate the first embodiment of the present invention. FIG. 14 shows the external appearance of the capsule-type endoscope of the fourth embodiment. FIG. 15 shows the internal structure of one of the capsule bodies. FIGS. 16A and 16B explain the operation in a state of usage. FIGS. 17A, 17B, 17C, and 17D illustrate the endoscopic examination procedure. FIG. 18 is a block-diagram illustrating the structure of electric systems of the external unit and display system. FIG. 19 is a block-diagram illustrating the structure of the external unit, which is a modification example of the fourth embodiment. FIGS. 20A to 20F are timing charts illustrating timing diagrams of illumination and image pickup in the embodiment employing the external unit shown in FIG. 19. FIG. 21 illustrates an example of antenna structure in another modification example of the fourth embodiment.

As shown in FIG. 14, a capsule-type endoscope 101 of the fourth embodiment of the present invention is composed of a capsule-shaped first capsule body 102A and a second capsule body 102B, each containing an image pickup device, and a soft thin strap 103 connecting back end sides of the two capsule bodies 102A, 102B.

In the present embodiment, the first capsule 102A and the second capsule 102B have the same structure. As an example, FIG. 15 shows the inner structure of the second capsule 102B.

In the second capsule 102B the front surface side of the body that has an almost cylindrical shape and is semi-spherically closed on the back end side thereof is covered with a semi-spherical transparent cover 105b.

An objective lens 106b is mounted in the center of the front surface portion of a body 104b inside the transparent cover 105b, and a CMOS image pickup device 107b serving as a solid-state image pickup element is disposed in the image forming position of the lens.

A plurality of LEDs 108b generating, for example, a white light are disposed around the objective lens 106b. LEDs 108b are driven by a LED drive circuit 109b provided inside the body 104b.

The image of the examinee located inside a somatic cavity and illuminated by the LEDS 108b is formed by the objective lens 106b on the CMOS image pickup device 107b serving as an image pickup element and disposed in the image forming position of the lens. This image is photoelectrically converted by the CMOS image pickup device 107b. The CMOS image pickup device 107b is driven by the drive signals from a driving and processing circuit 111b, conducts signal processing by extraction and compression of image signal components with respect to photoelectrically converter output signals, and sends the signals to a transmission circuit 112b.

The transmission circuit 112b conducts high-frequency modulation of the input image signals, converts them into high-frequency signals, for example, with a frequency of 2.4 GHz, and emits electromagnetic waves from an antenna 113b to the outside. Power necessary for an operation of the transmission circuit 112b, driving and processing circuit 111b, and LED drive circuit 109b is supplied from a battery 114b.

Structural components of capsule body 102A corresponding to structural components of capsule body 102B explained with reference to FIG. 15 will be explained below by using reference symbols (a) instead of reference symbols (b). Furthermore, structural components identical to those explained in FIG. 15 are shown, for example, in FIG. 24.

In the present modification, transmission from a transmission circuit 112a of capsule body 102A and transmission circuit 112b of capsule body 102B is conducted by slightly changing the transmission frequency. The signals are received by an external unit 116 (see FIG. 17A) disposed outside.

In other words, electromagnetic waves transmitted by antennas 113a and 113b connected to the transmission circuit 112a of the capsule body 102A and transmission circuit 112b of the capsule body 102B, respectively, are received by the external unit 116 shown in FIG. 17A.

FIG. 17A shows how a patient 117 swallows the capsule 101 when the endoscopic examination is begun. In this case, since the picked-up image signals are transmitted by the capsule-type endoscope 101 as electromagnetic waves, those electromagnetic waves are received by the external unit 116 mounted, for example, with a belt of the patient 117 at a waist line of the patient 117 and stored in the memory located inside the external unit 116.

When the endoscopic examination with the capsule-type endoscope 101 is completed, the external unit 116 is installed in a data capture unit 119 provided in a display system 118 shown in FIG. 17B, and the image data accumulated in the external unit 116 can be imported in the display system 118 via the data capture unit 119.

FIG. 18 shows the configuration of the electric systems of the external unit 116 and display system 118.

The external unit 116 serving as a receiver comprises two antennas 121a, 121b receiving with good efficiency the electromagnetic waves of the frequency transmitted by the antennas 113a, 113b of the capsule bodies 102A and 102B, and the high-frequency signals induced in the antennas 121a, 121b are input in respective receiving circuits 122a, 122b.

The receiving circuits 122a, 122b are controlled by respective control circuits 123a, 123b, and the control circuits 123a, 123b demodulate the high-frequency signals received by the receiving circuits 122a, 122b and conduct control so that those signals are successively stored in a memory 124.

The memory 124 is composed of a hard disk (abbreviated as HDD in the figure). The memory 124 is connected to a connector 125. When the external unit 116 is installed in the data capture unit 119 shown in FIG. 17B, a connector 125 is connected to a connector 126 of data capture unit 119, as shown in FIG. 18.

The connector 126 is connected to a memory 130 of display system 118. The memory 130 is controlled by a control circuit 131. The image data of observed images that are accumulated in the memory 124 of external unit 116 are developed and processed by an image processing circuit 132 via the memory 130 and stored, that is, recorded in a memory 133 which is a recording unit.

The memory 133 is, for example, composed of a hard disk. The memory 133 is connected to a display circuit 134 conducting display processing, and image signals sent to the display circuit 134 are displayed by a display unit 136 conducting display of images as captured images via a comparison circuit 135 conducting comparison. The comparison circuit 135 is connected to a disease image database (abbreviated as DB) 137, compares the images from the disease image database 137 with the captured image, retrieves a similar past disease image, and simultaneously displays it on the display unit 136 as the DB image.

Furthermore, the control circuit 131 is connected to a console 138 such as a keyboard, and the command to capture images, to input patient data, to input diagnostic results, and the like are conducted from the console 138.

A specific feature of this embodiment, as shown in FIG. 14, is that the back ends of the two capsule bodies 102A, 102B, which are opposite to the front ends covered with transparent covers 105a, 105b are connected with a flexible strap 103 that has a width sufficiently less than that of the outer diameter of those capsule bodies 102A, 102B and such a structure allows for illumination and image pickup in mutually opposite directions.

The operation relating to this embodiment will be described below.

When endoscopic examination is conducted, the external unit 116 is attached to the waste of the patient 117, for example, as shown in FIG. 17A, and the patient 117 is asked to swallow the capsule-type endoscope 101.

The capsule-type endoscope 101, for example, after the preset time, conducts illumination and image pickup, the picked-up image signals are transmitted from the antenna 113a, 113b, and the external unit 116 receives the transmitted image signals and stores them in the memory 124.

FIGS. 16A and 16B show how the images of the inside, for example, of a large intestine 140 are picked up with the capsule-type endoscope 101.

In the present embodiment, the two capsule bodies 102A, 102B are connected by the thin flexible strap 103. Therefore, even when examination is conducted inside a lumen, for example, a right colon curve, as shown in FIG. 16A, the endoscope can be freely bent in strap 103. Therefore, the endoscope can smoothly advance the inside of the lumen, similarly to a single-capsule-type endoscope. Therefore, examination can be conducted without causing paint or discomfort to the patient 117.

Furthermore, in the present embodiment, the capsule bodies 102A, 102B have a structure such that the sides opposite to the back ends linked by the strap 103 serve as illumination and image pickup sides. Therefore, for example, as shown in FIG. 16A, there may be instances when a portion 140 shown by dotting becomes a dead zone whose image cannot be picked up by the capsule body 102B, which is located in the zone ahead in the movement direction, due to half-moon folds. However, following this state, as shown in FIG. 16B, illumination and image pickup with the illumination and image pickup devices of the other capsule 102A is conducted from the direction opposite to that of the preceding capsule 102B, and the image of the zone that was a dead zone for the preceding capsule can be picked up with the succeeding capsule 102A.

Thus, with the present embodiment, the occurrence of portions becoming the dead zones is prevented to a greater degree than with a single capsule body and effective images can be obtained.

Image signals obtained from two capsule bodies 102A, 102B are accumulated in the memory 124 of the external unit 116, and after the capsule-type endoscope 101 is discharged to the outside of body, the external unit 116 is installed in the data capture unit 119 shown in FIG. 17B and the command signal of image capture is input from the console 138 of the display system 118.

In such a case, the image data accumulated in the memory 124 of the external unit 116 are transferred into the image processing circuit 132 via the memory 130 functioning as a buffer, subjected to processing such as development, and accumulated one by one as image data in memory 133.

The image data stored in the memory 133 can be successively displayed on the display device 136 if a display command is input from the console 138 by an operator.

Furthermore, when a command input was made to pick up the image similar to the disease image that was accumulated in the disease database 137 with respect to the captured image, the image that was captured by the capsule-type endoscope 101 is displayed together with the disease image from the disease database 137 on the display surface of display device 136, as shown in FIG. 17C. In this state, the control circuit 131 shown in FIG. 18 conducts a comparative processing such as pattern matching of the captured image and the disease image read out from the disease database 137 with the comparison circuit 135 and makes a decision as to whether there is a similarity exceeding the preset ratio. If a decision is made that there is a similarity exceeding the preset ratio, this image together with several adjacent images are linked to the data of disease database 137 and stored in the memory 133.

Then, only the images that can be related to a disease are extracted from all of the captured images and stored, for example, in an image extraction folder of the memory 133.

As shown in FIG. 17D, the operator then conducts command input from the console 138 so as to display the extracted image on the display device 136. As a result, the images stored in the image extraction folder are displayed successively and the operator can conduct final diagnostics with good efficiency. Thus, using the database to assist the diagnostics allows the diagnostics to be half automated and makes possible a significant reduction of time spent by the doctor on examination.

With the present embodiment, the illumination devices and image pickup devices are provided in both capsules. Therefore, the observation direction can be the same as the movement direction and observations can be simultaneously conducted ahead and behind in the movement direction. As a result, the endoscope can be moved more smoothly inside curved lumens in a body than in the conventional examples and images can be picked up without causing strong pain in the patient, and from different directions, more specifically, from the movement direction and the direction opposite thereto. Therefore, high-quality images can be obtained and the number of occurring dead zones is small. Furthermore, a set of images captured inside the body can be obtained and, thus, the operator saves such a time of picking up images while inserting the endoscope.

FIG. 19 illustrates the structure of a modification example of the external unit 116.

The external unit 116 shown in FIG. 18 comprised the two antennas 121a, 121b, receiving circuits 122a, 122b, and control circuits 123a, 123b. In the present modification example, the external unit comprises single antenna 121, a receiving circuit 122, and a control circuit 123.

Further, in the present modification example, as shown in FIGS. 20A to 20F, the timings at which the transmission circuits 112a, 112b transmit the images obtained by illumination and image pickup by two capsule bodies 102A, 102B are shifted by half a period (T/2) with respect to each other to avoid overlapping thereof.

In other words, when the power supply of the two capsule bodies 102A, 102B is turned ON and they are set into the operation state, for example, a LED 108a of the capsule body 102A is ignited for a short time (for example, 1/30 sec) and an image is picked up by the CMOS image pickup device 107a and transmitted by the transmission circuit 112a (almost within half a period, T/2).

Once the transmission by the transmission circuit 112a has been completed, the LED 108b of the other capsule body 102B is ignited for a short time, an image is picked up by the CMOS image pickup device 107b and transmitted by the transmission circuit 112b. Once the transmission by the transmission circuit 112b has been completed, the LED 108a of he first capsule body 102A is again ignited.

With such an operation, the image signals transmitted by the transmission circuits 112a, 112b are received by one antenna 121, received by the receiving circuit 122, and stored in the memory 124.

In this case, when the transmission frequencies of the transmission circuits 112a and 112b are slightly different, they can be received with a sufficiently good efficiency by the same antenna 121. Furthermore, based on the transmission frequency, the external unit 124 can decide which of the image pickup elements has picked up the image.

Further, when the transmission circuits 112a and 112b transmit at the same frequency, transmission may be conducted as shown in FIGS. 20A to 20F. In this case, he transmission may be conducted by adding an identification code, for example, to the header of the image which is to be transmitted.

In this case, the identification code may be recognized by the external unit 116 and separated from the image data, followed by storage in the memory 124, or the image data may be stored in the memory 124, with the identification code attached thereto, and the identification code may be recognized and separated from the image data in the display system 118.

FIG. 21 shows an antenna of the modification example of external unit 116. In the present modification example, the external unit 116 installed in a belt is connected with a connection cable 142 to a necktie-type antenna row 144 located on a shirt 143 that is worn by the patient 117. This necktie-type antenna row 144 is detachably secured to the shirt 143 with a button 145.

The necktie-type antenna row 144 thus hangs down from the neck of the patient 117, and the antenna of the most intensive electromagnetic wave received among a plurality of antennas 144a constituting the antenna row 144 is used.

With the present modification example, the installation can be conducted in an easy manner, without intensifying the pressure on the patient 117. Further, a plurality of antennas 144a are arranged in the vertical direction and located in the vicinity of the center in the width direction of the body of patient 117. Therefore, as the capsule-type endoscope 101 descends by peristalsis, since a plurality of antennas 144a are present along this direction, signals can be effectively received by the closest antenna 144a.

The first modification example of the present embodiment will be described below with reference to FIG. 22.

Figure 22:
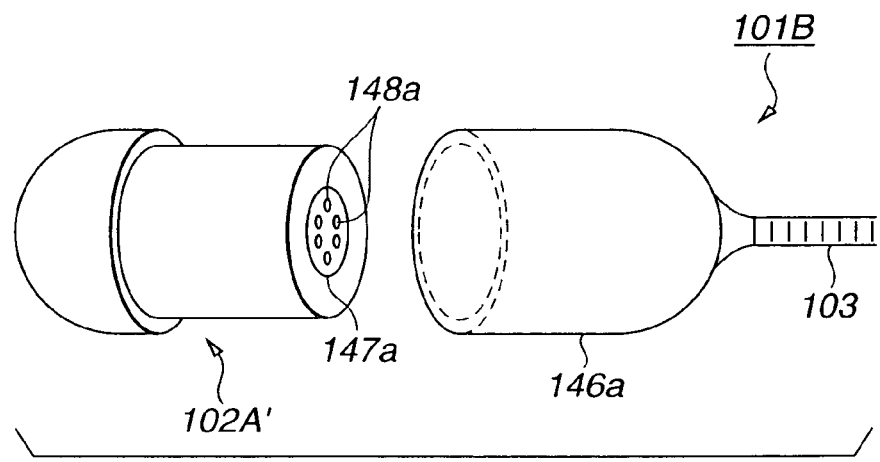
FIG. 22 is a perspective view illustrating a part of the capsule-type endoscope of the first modification example of the fourth embodiment.

In the capsule-type endoscope 101B of modification example shown in FIG. 22, the external portion of the capsule body 102A shown in FIG. 14 can be removed as a cover 146. An electrode 148 of a communication port 147 is exposed in the back end of a capsule body 102A' from which the cover 146 has been removed.

Figure 23:
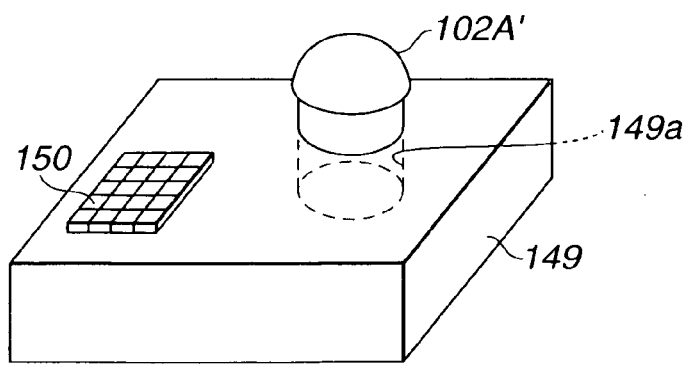
FIG. 23 illustrates the state in which the cover of capsule-type endoscope shown in FIG. 22 was removed and the capsule body is installed in a rewriting device.

As shown in FIG. 23, the back end of the capsule body 102A' from which the cover 146 has been removed is installed in a connector socket 149a of a rewriting unit 149, and the operation program located inside the capsule body 102A' can be changed by manipulating the input keys 150 of the rewriting unit 149.

Figure 24:
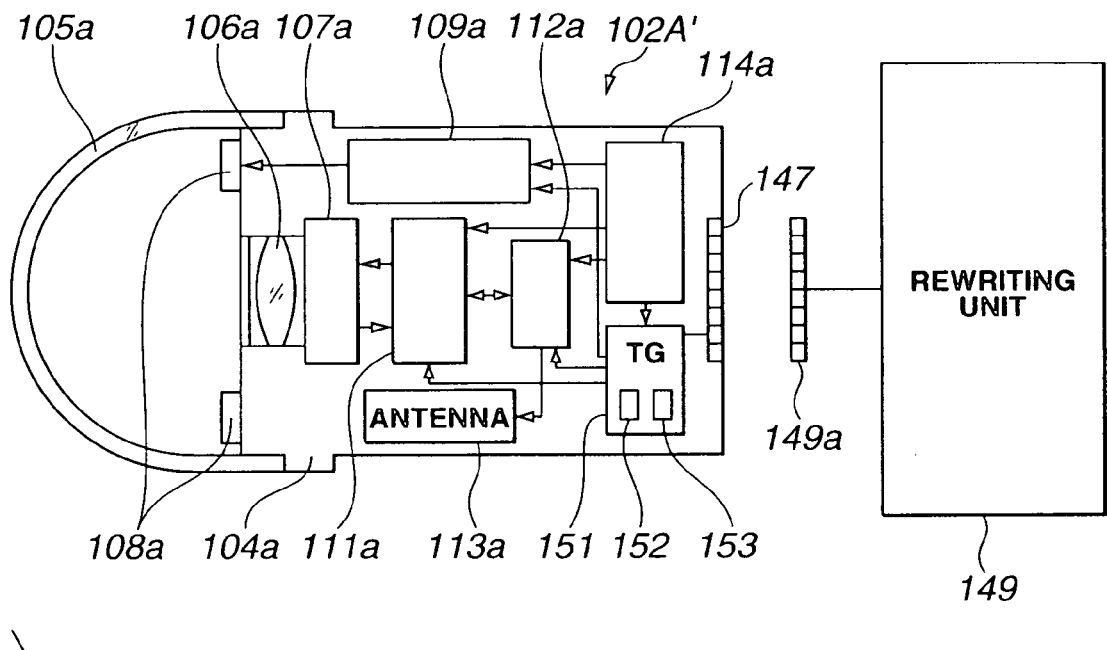
FIG. 24 illustrates the internal structure of the capsule body shown in FIG. 22.

FIG. 24 illustrates the rewriting unit 149 and the internal structure of the capsule body 102A' in this case, that is, when the cover 146 has been removed. In the fourth embodiment, the capsule body 102A' additionally comprises a timing control circuit for conducting timing control or a timing (abbreviated as TG in FIG. 22 and elsewhere) generator 151 and the above-mentioned communication port 147 connected to the timing generator 151.

A CPU 152 conducting control operation and a memory 153 such as a flash memory having written therein a program determining the control operation of the CPU 152 are provided inside the timing generator 151, and the contents of programs thereof can be rewritten by connecting to the rewriting unit 149. The other capsule body 102B has the same structure.

The operation is described below.

Prior to using the endoscope for endoscopic examination, the cover 146 is removed and the capsule body 102A' is set into the rewriting unit 149, as shown in FIG. 23. Then, input keys 150 are manipulated and the rewriting unit 149 sends data such as driving timing of illumination and image pickup or illumination period to the timing generator 151 of capsule body 102A' via the communication port 147.

The CPU 152 of timing generator 151 rewrites the data in memory 153 with the transmitted data. Thus, the CPU 152 serving as a setting unit can randomly set from the outside the settings required for the realization of functions in at least one of the illumination device, observation device, wireless transmission unit, and control unit.

The capsule body 102A' is thereafter disconnected from the rewriting unit 149, and the cover 146 is attached. Further, the same operation is conducted with respect to the other capsule body 102B'. The patient 117 is then asked to swallow the capsule-type endoscope 101B.

Illumination and image pickup are then conducted at the illumination and device timing set by manipulating the input keys 150.

As a specific example of data that are written, for example, when mainly the large intestine of the patient 117 is examined, the settings are made such that one frame image is picked up in 2 seconds within 6 hours after the capsule-type endoscope 101B was swallowed and two frame images are picked up in 1 second after the 6 hours have elapsed.

In such a modification example, a frame rate can be increased to conduct detail observation, for example, in the zone where the patient's symptoms are suspicious, so as to obtain a large number of images in the zone which requires careful examination based on the patient's symptoms. In other words, the operator can freely set the image pickup conditions according to the zone which is to be examined, thus, effective picked-up images can be obtained, and the consumption of battery energy can be reduced.

Figure 25:
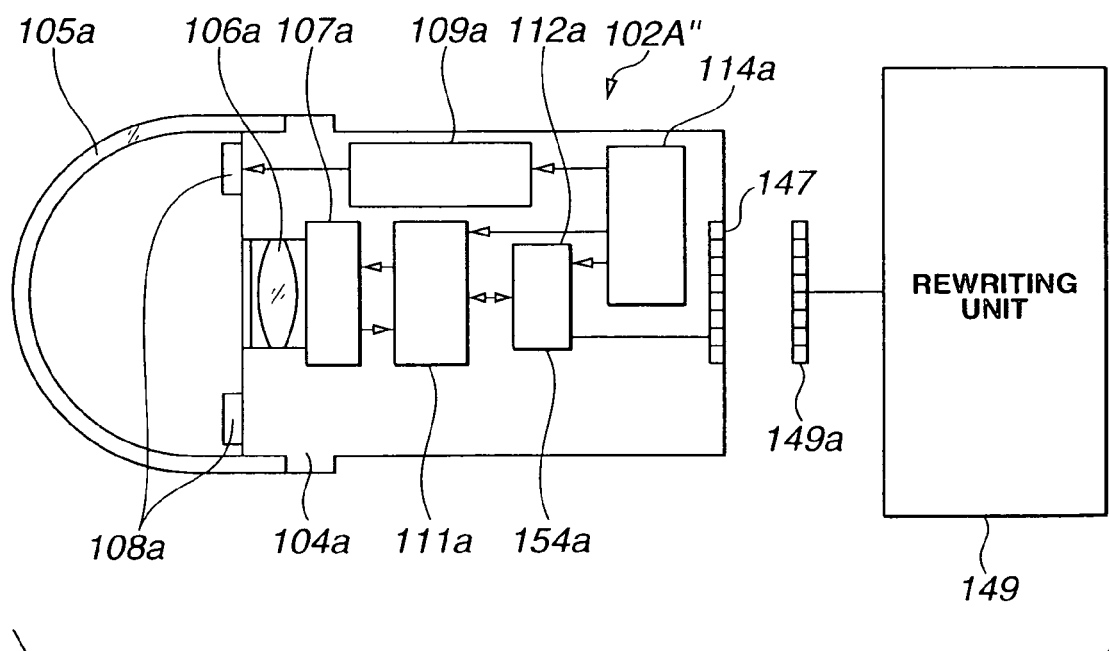
FIG. 25 illustrates the internal structure of the capsule body in the second modification example of the fourth embodiment.

FIG. 25 shows a capsule body 102A" of the second modification example. In the structure of this capsule body 102A", a drive and processing circuit 111a shown in FIG. 24 is connected to a memory 154a and the memory 154a is connected to a communication port 147a.

Data on the patient which is to be examined can be input into the memory 154a by the rewriting unit 149 prior to endoscopic examination.

Furthermore, image data picked up by the driving and processing circuit 111a are accumulated in the memory 154a during endoscopic examination. Once the endoscope capsule has been recovered, the image data accumulated in the memory 154a are read out together with the patient's data by a display system provided with a communication port connectable to the communication port 147a. As a result, the image data can be managed in a state in which the relationship thereof with the patient's data is maintained.

In the first modification example shown in FIG. 24, a memory storing the patient's data may be also provided, and when the image data are transmitted, the patient's data stored in the memory may be initially transmitted as header information of the image data.

Fifth Embodiment

Figure 26:
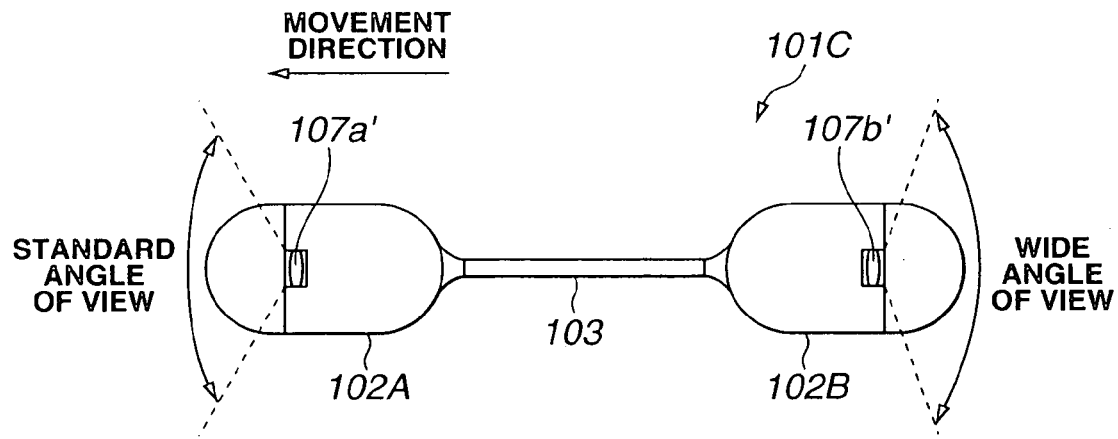
FIG. 26 schematically illustrates the capsule-type endoscope of the fifth embodiment of the present invention.

The fifth embodiment of the present invention will be described below with reference to FIGS. 26 to 28. FIG. 26 shows a capsule-type endoscope 101C of the fifth embodiment. In the capsule-type endoscope 101C, for example, the objective lenses 106a, 106b of capsule bodies 102A, 102B of the fourth embodiment are replaced with an objective lens 107a' with a standard angle of view and an objective lens 107b' with a wide angle of view. For sake of simplicity, only the objective lens 107a' and objective lens 107b' are shown in FIG. 26. The same is true for FIG. 27 described hereinbelow.

In this case, an angle of view providing for an observation field of view from 120° to 140° is set as a standard angle of view, and an angle of view providing for an observation field of view from 160° to 180° is set as the wide angle of view.

Further, the movement direction in case of endoscopic examination with the capsule-type endoscope 101C is such that the images are first picked up with the objective lens 107a' with the standard angle of view. Otherwise the structure is identical to that of the fourth embodiment. The observation devices of each hard unit have objective optical systems with mutually different angles of field of view.

With the present embodiment, overlooking can be reduced by conducting far-point observations with the objective lens 107a' with a standard angle of view in the capsule body 102A located ahead zone in the movement direction and conducting near-point observations with the objective lens 107b' with a wide angle of view in the rear capsule body 102B.

Figure 27:
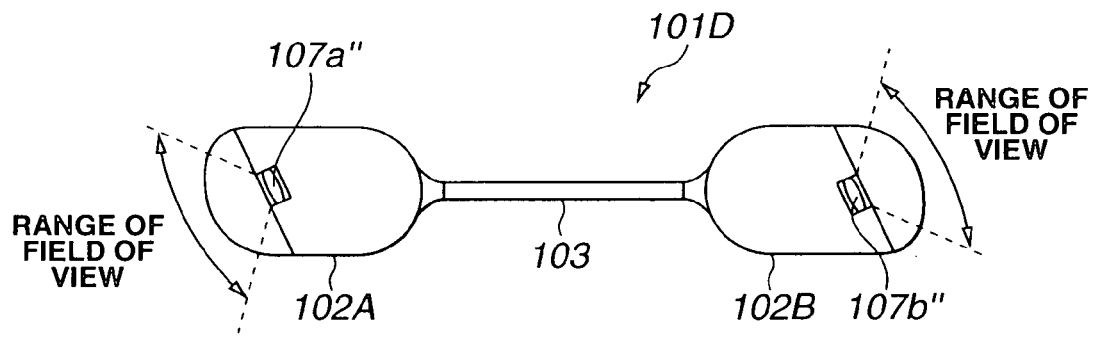
FIG. 27 schematically illustrates the capsule-type endoscope of the first modification example of the fifth embodiment of the present invention.

FIG. 27 shows a capsule-type endoscope 101D of the first modification example. In this capsule-type endoscope 101D, the devices conducting illumination and image pickup in the direct-viewing direction of capsule bodies 102A, 102B in the fourth embodiment are modified so as to conduct illumination and image pickup in the directions inclined to the movement direction of capsule-type endoscope 101D.

In case of the structure shown in FIG. 27, the fields of view of objective lenses 107a", 107b" are defined by directions inclined in the mutually opposite directions with respect to the movement direction of capsule-type endoscope 101D. For example, if the field of view of objective lens 107a" is inclined downward, then the field of view of the other objective lens 107b" is inclined upward.

With the present modification example, since the inclined viewing directions are different ahead and behind the endoscope, the lumens can be observed within a wider range by combining the images obtained with both lenses.

Figure 28:
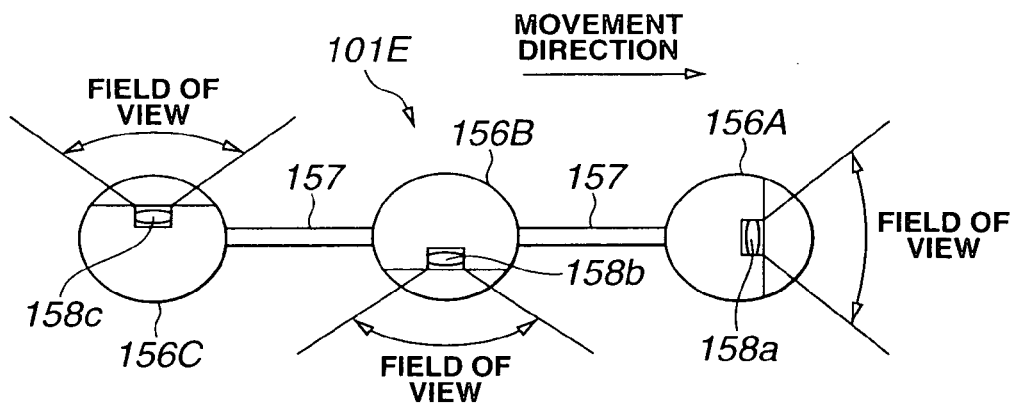
FIG. 28 schematically illustrates the capsule-type endoscope of the second modification example of the fifth embodiment of the present invention.

FIG. 28 shows a capsule-type endoscope 101E of the second modification example. This capsule-type endoscope 101E has a structure in which three capsule bodies 156A, 156B, and 156C are linked by a thin flexible strap 57. Further, the capsule 156A has an objective lens 158a with a field of view in the direct-viewing direction, the capsule body 156B has an objective lens 158b with a field of view in the downward side-viewing direction, and the capsule 156C has an objective lens 158c with a field of view in the upward side-viewing direction.

With this modification example, the inside of lumens can be observed within even wider range by combining the images obtained with all of the capsule bodies.

Sixth Embodiment

The sixth embodiment of he present invention will be described hereinbelow with reference to FIG. 29, FIG. 30A, and FIG. 30B. FIG. 29 shows a capsule-type endoscope 101F of the sixth embodiment. In the capsule-type endoscope 101F, a toggle switch 161 and a charge accumulation circuit 162 are provided as the LED drive circuit 109a in the capsule-type endoscopes 102A' and 102B', for example, in the capsule-type endoscope 101B shown in FIG. 22. Only one capsule body 102A is shown in FIG. 29.

Further, a transmission-receiving circuit 112a' is employed instead of the transmission circuit 112a. If a switch operation signal Sk is sent from the outside, it is received by the antenna 113a, demodulated by the transmission-receiving circuit 112a', and sent to a CPU 152a of timing generator 151a. The CPU 152a conducts control operation according to the switch operation signal Sk.

More specifically, the LED 108a, as shown in FIG. 30A and FIG. 30B, intermittently emits light under the effect of electric power of battery 114a. However, if the switch operation signal Sk is received, the CPU 152a of timing generator 151a switches the toggle switch 161a so that it is connected to the charge accumulation circuit 162a. As a result, the electric power accumulated in the charge accumulation circuit 162a is supplied to the LED 108a and a large quantity of light is emitted.

With the present embodiment, for example, when the capsule-type endoscope 101F reaches the position which apparently requires careful examination, transmitting the switch operation signal Sk from the outside makes it possible to cause the emission of a large quantity of light by the LED 108a and to obtain a bright image with a good S/N ratio.

More specifically, even when the LED 108a is caused by the battery 114a to emit light inside the esophagus or small intestine, a sufficiently bright image can be obtained. However, inside the stomach or large intestine, the illumination light is not fully received and dark images are sometimes obtained.

If a switch operation signal Sk is sent from the outside with respect to the zones for which dark images are obtained, for example, zones that are apparently the affected areas, then the entire electric power that was charged into the charge accumulation circuit 162 within the sufficient period of time is supplied via the toggle switch 161 as a large electric current into the LED 108a, and a large quantity of light is emitted instantaneously. As a result, a bright image, even if still image, with a good S/N ratio can be obtained in the desired zones inside the stomach and large intestines.

Further, since the LED 108a generates heat, illumination in usual observations is conducted at an electric current of no higher than a standard value. However, the LED 108a practically does not degrade even if a large electric current such as reaching the standard value is passed instantaneously therethrough.

In the present embodiment, the amount of illumination light was switched by the switch operation signal Sk. However, a configuration may be also used in which the illumination and image pickup periods can be changed by the switch operation signal, that is, the operation periods of a plurality of illumination devices and observation devices can be changed by the switch operation signal from the outside.

Seventh Embodiment

Figure 31:
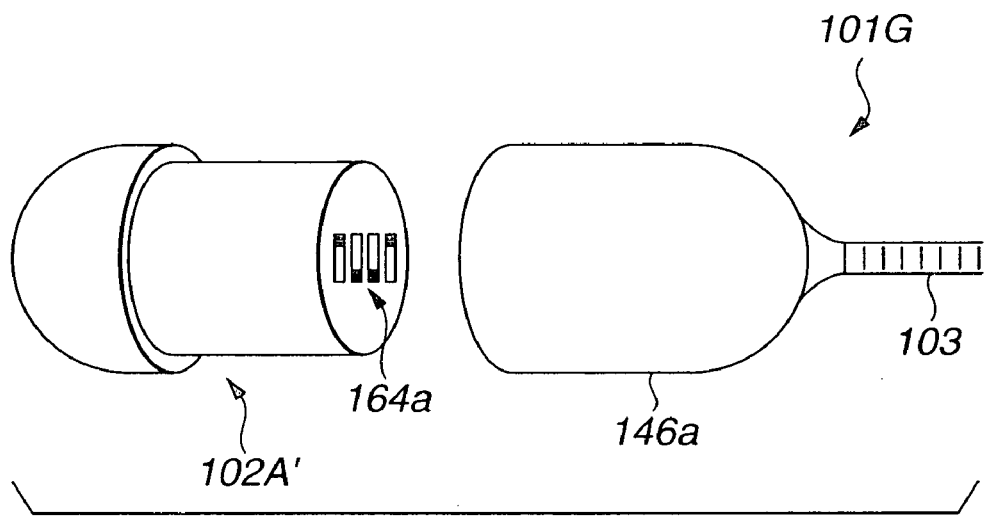
FIG. 31 explains a part of configuration of the capsule-type endoscope of the seventh embodiment of the present invention.

The seventh embodiment of the present invention will be described below with reference to FIG. 31 and FIG. 32. FIG. 31 shows a capsule-type endoscope 101G of the seventh embodiment. In this capsule-type endoscope 101G, a dip switch 164a is provided instead of the communication port 147a shown in FIG. 22 and the transmission frequency of the internal transmission circuit can be variably set by the dip switch 164a.

With this embodiment, even if a plurality of capsule-type endoscopes 101G are swallowed, setting different frequencies for the transmission of image signals by each endoscope makes it possible to recognize and manage the signals during receiving.

Figure 32:
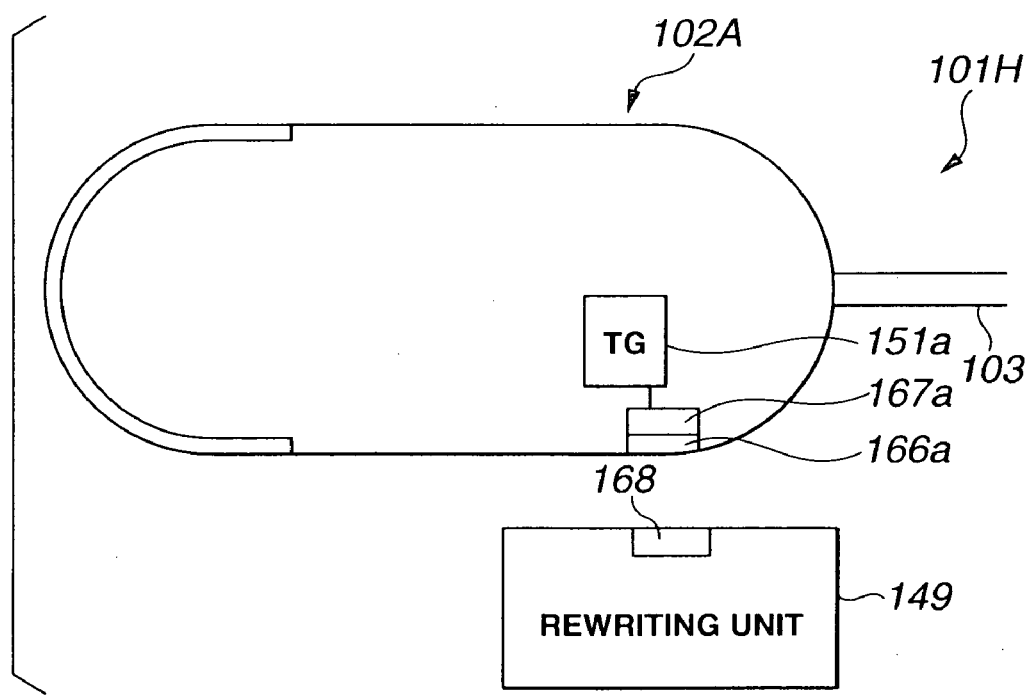
FIG. 32 illustrates a part of configuration of the capsule-type endoscope of the modification example of the seventh embodiment of the present invention.

FIG. 32 shows a capsule-type endoscope 101H of the modification example of the seventh embodiment. In this capsule-type endoscope 101H, an infrared radiation (IR) port 167a is provided on the inner side of a transparent cover glass 166a provided on the external surface in the capsule body 102A, for example, shown in FIG. 29.

The communication is conducted with infrared radiation and the IR port 168 provided in the rewriting unit 149. Further, in this modification example, the cover 146 is not separated. With this modification example, setting of illumination and image pickup timing can be conducted even without connecting to the rewriting device 149. Thus, the CPU conducts those settings by using remote communication such as infrared radiation communication and the like. Otherwise, the effect obtained is almost identical to that explained with reference to FIG. 29.

Eighth Embodiment

Figure 33:
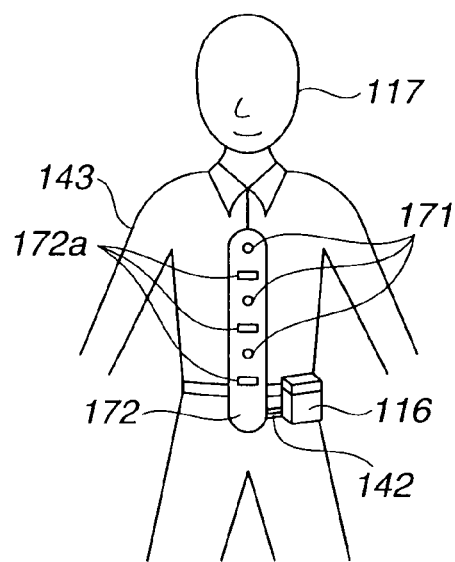
FIG. 33 illustrates the structure of the antenna of the external unit of the eighth embodiment of the present invention.

The eighth embodiment of the present invention will be described hereinbelow with reference to FIGS. 33 to 35. FIG. 33 shows a structure relating to the antenna of external unit 116. In this embodiment, a stripe-like antenna row 172 is attached to the front button 171 portion of a shirt 143 of the patient 117. A plurality of antennas 172a constituting the antenna row 172 are connected to the external unit 116 with a connection cable 142.

The operation and effect of this embodiment are almost identical to those explained with reference to FIG. 21.

Figure 34:
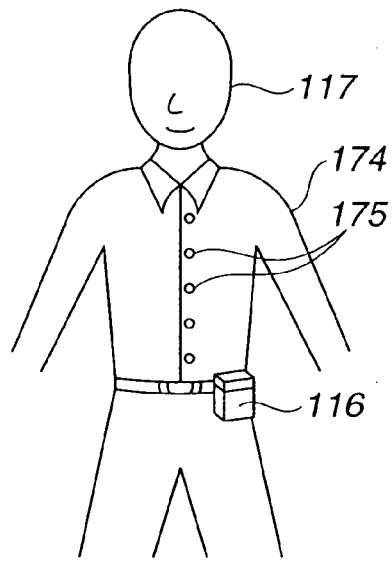
FIG. 34 illustrates the structure of the antenna of the first modification of the eighth embodiment of the present invention.

FIG. 34 shows the first modification example of the eighth embodiment. In FIG. 34, a shirt 174 incorporates the antenna row. Buttons 175 also function as antennas.

Figure 35:
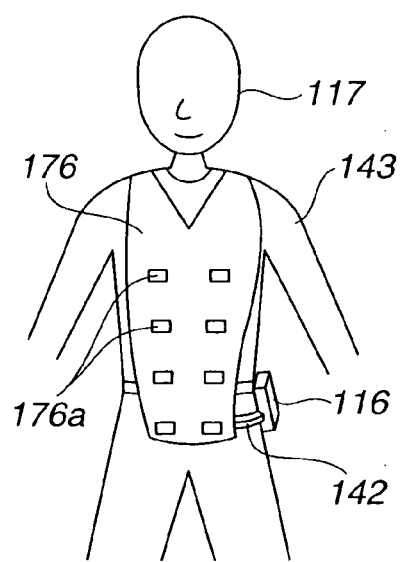
FIG. 35 illustrates the structure of the antenna of the second modification of the eighth embodiment of the present invention.

FIG. 35 shows the second modification example of the eighth embodiment. In FIG. 35, an apron-like antenna row 176 is in the form of an apron put on the shirt 143. A plurality of antennas 176a are provided in the apron-like antenna row 176. The operation and effect of this embodiment are almost identical to those explained with reference to FIG. 33.

Ninth Embodiment

Figure 36B:
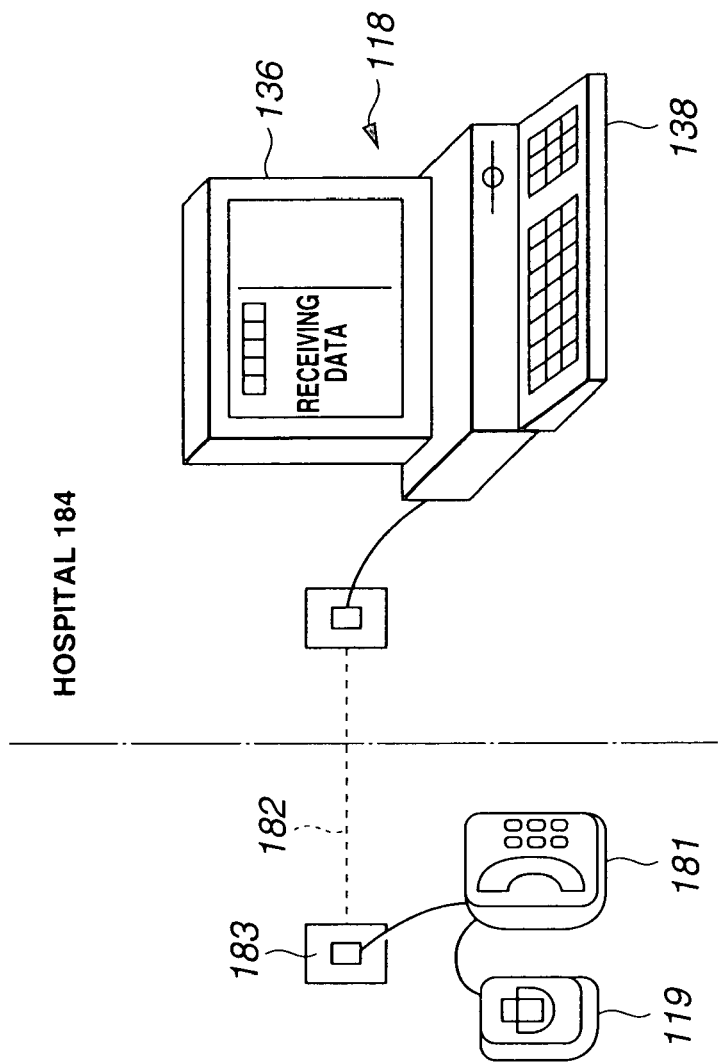
FIG. 36A and FIG. 36B explain the structure of the capsule-type endoscopic system of the ninth embodiment of the present invention.
Figure 36A:
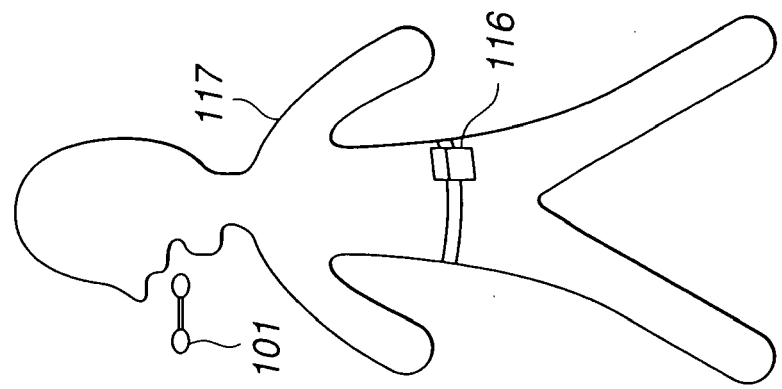
Figure 37:
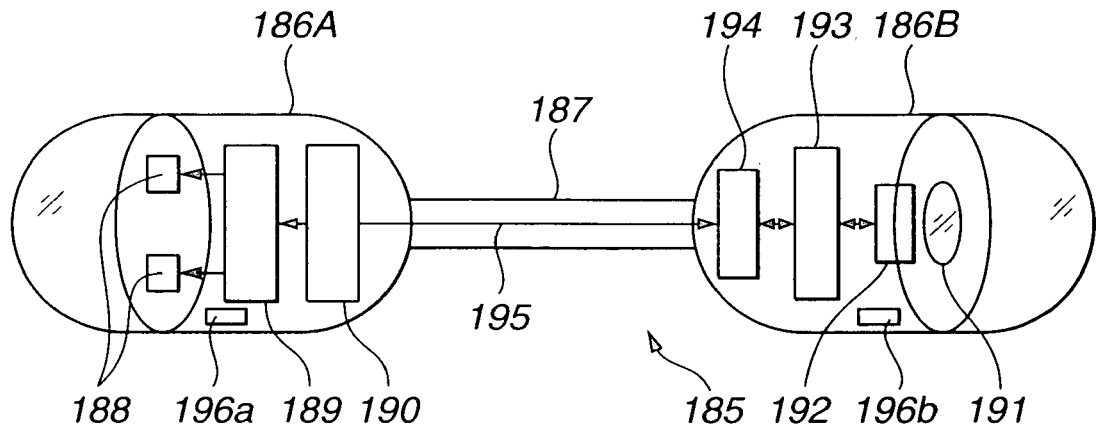
FIG. 37 illustrates the structure of the capsule-type endoscope of the tenth embodiment of the present invention.

The ninth embodiment of the present invention will be described hereinbelow with reference to FIGS. 36A and 36B. FIGS. 36A and 36B illustrate a state of endoscopic examination of the ninth embodiment. FIG. 36A relates to the initial stage of examination. FIG. 36B illustrates how the images obtained in the course of the examination are transmitted from the patient's home to the hospital.

In this embodiment, the data capture unit 119, for example, installed in the external unit 116 is connected to a connection unit 183 of a telephone line 182 connected to a telephone 181, and further connected to the display system 118 disposed in a hospital 184 via the telephone line 182.

Otherwise, the configuration is identical to that of the fourth embodiment.

As for the operation of this embodiment, when endoscopic examination is conducted, as shown in FIG. 36A, the patient 117 swallows the capsule-type endoscope 101.

Image data obtained with capsule-type endoscope 101 are accumulated in the external unit 116. Upon completion of the endoscopic examination, the external unit 116 is connected to the data capture unit 119 connected to the telephone line 182 and the image data are automatically transferred to the hospital or other remote site via the telephone line 182.

In the hospital, the image data are received and automatically imported. The final diagnostics is conducted by the doctor.

In this embodiment, diagnostics is possible even when the patient is in a remote location far from a hospital. Furthermore, since the examination of the patient can be conducted not only in a hospital, the degree of freedom of patient 117 is increased.

Further, the transmission of image data is not limited to that via the telephone line and wireless transmission may be also conducted. Moreover, the transmission may be conducted with other communications means such as cellular phones, internet, and the like.

Tenth Embodiment

The tenth embodiment of the present invention will be described hereinbelow with reference to FIGS. 37 to 42. In this embodiment, illumination and image-pickup functions are separated between a plurality of capsule bodies, and illumination and image pickup are conducted by combining the operations of the capsule bodies. In a capsule-type endoscope 185 of the tenth embodiment shown in FIG. 37, a capsule body 186A and capsule body 186B are connected with a strap 187.

Further, a LED 188 emitting white light, a LED drive circuit 189, and a battery 190 are enclosed in the capsule body 186A. An objective lens 191, a CMOS image pickup device 192, a drive and processing circuit 193, a transmission circuit 194, and an antenna (not shown in the figure) are enclosed in the other capsule body 186B. The capsule bodies 186A, 186B are connected with a signal line 195.

Figure 38:
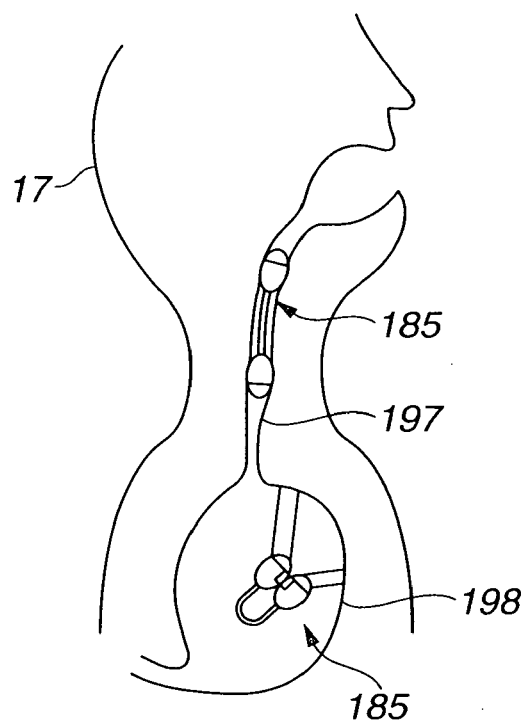
FIG. 38 explains endoscopic examination of the tenth embodiment of the present invention.

Magnets 196a, 196b are provided inside the capsule bodies 186A, 186B, respectively. As shown in FIG. 38, the capsule bodies can be easily attracted to each other by magnetic forces of magnets 196a, 196b serving as joining components. Therefore, the two capsules are joined in the prescribed position.

FIG. 38 illustrates the operation of the present embodiment. When endoscopic examination of the patient 117 is conducted, the patient is asked to swallow the capsule-type endoscope 185 straightened out into a line.

When the endoscope passes through a narrow lumen portion of an esophagus 197, the endoscope advances to a deeper region, while maintaining the linear shape. If it then reaches a wide zone, such as a stomach 198, the two capsule bodies 186A, 186B are drawn close to each other by the magnetic forces of the magnets 196a, 196b.

Illumination and image pickup (including the function of transmitting the image signals) are then conducted in such a state. At least one of the capsule bodies is provided with a magnetic sensor, such as a Hall element, for detecting the state in which the capsule bodies are combined by magnetic forces of the magnets 196a, 196b, and the control initiating the illumination and image pickup based on the detection output of the sensor is conducted by a control unit (not shown in the figures). Alternatively, as shown in FIG. 24, illumination and image pickup may be conducted after the prescribed time has elapsed, or as shown in FIG. 29, the operation control may be conducted based on the external signals.

With the present embodiment, image signals can be can be obtained by improving the illumination and image pickup functions executed by the capsule bodies. For example, high-resolution images with good S/N ratio can be obtained by increasing the quantity of illumination light or increasing the number of pixels in the image pickup element.

Figure 39A:
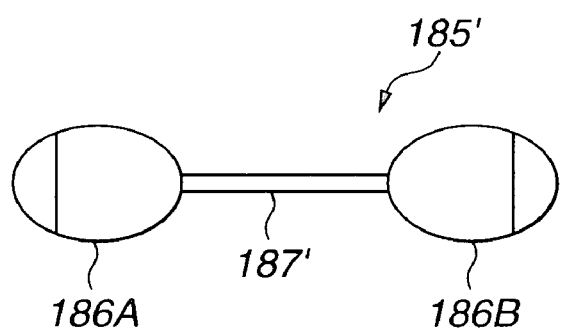
FIG. 39A and FIG. 39B explain the structure of the capsule-type endoscope of the first modification of the tenth embodiment of the present invention.
Figure 39B:
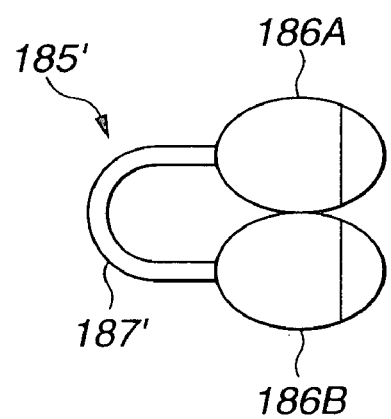

FIGS. 39A and 39B show a capsule-type endoscope 185' of the first modification example. The magnets 196a, 196b are not used in the capsule-type endoscope 185' and a strap 187' formed from a shape memory material is employed as the strap 187 serving as a joining member.

In this case, the strap 187' formed from a shape memory material was subjected to shape memory processing such that it has a linear shape at room temperature, as shown in FIG. 39A, but is bent, as shown in FIG. 39B, if the temperature becomes no less than the body temperature, thereby combining the two capsule bodies 186A, 186B. In this case, too, the operation and effect are almost identical to those explained with reference to FIG. 37.

Figure 40A:
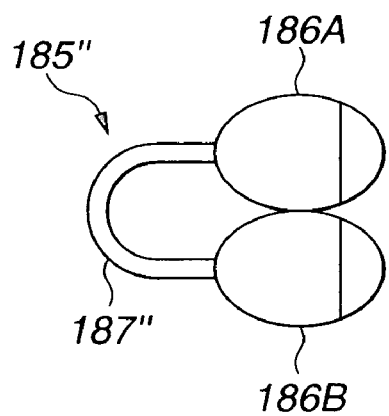
FIG. 40A and FIG. 40B explain the structure of the capsule-type endoscope of the second modification of the tenth embodiment of the present invention.
Figure 40B:
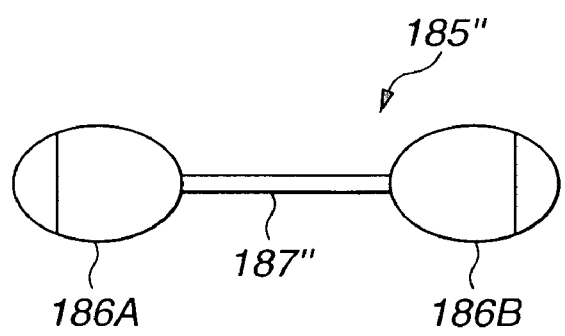

FIGS. 40A and 40B show a capsule-type endoscope 185" of the second modification example. In the capsule-type endoscope 185", a strap 187" is formed from a spring material processed (impelled) so as to be bent and to combine the two capsule bodies 186A, 186B, as shown in FIG. 40A. When the endoscope is swallowed, the strap is straightened out, as shown in FIG. 40B. In this case, too, the operation and effect are almost identical to those explained with reference to FIG. 37.

Figure 41:
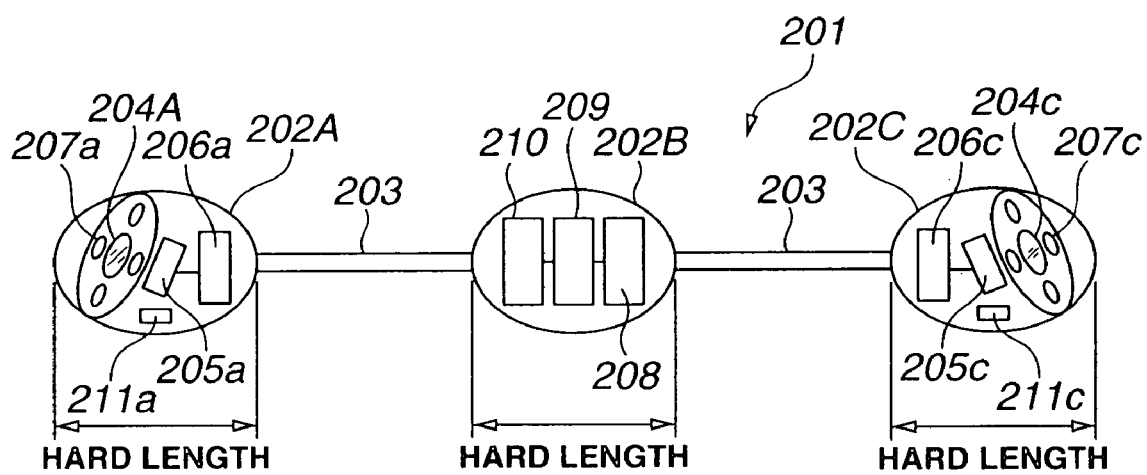
FIG. 41 illustrates the structure of the capsule-type endoscope of the third modification of the tenth embodiment of the present invention.

FIG. 41 shows a capsule-type endoscope 201 of the third modification example. In this modification example, combining the capsules improves the illumination and image pickup function, more specifically, the image pickup range, over those obtained when the capsules are not combined.

In the capsule-type endoscope 201, three capsule bodies 202A, 202B, 202C are linked with a thin soft strap 203. The capsule body 202A and other capsule bodies are hard and have a hard length shown in the figure.

The objective lenses 204a, 204c with a field of image view inclined upward are enclosed in transparent covers in the respective capsule bodies 202A, 202C on both end sides, and image pickup elements 205a, 205c are disposed in image forming positions of respective lenses. The image pickup elements 205a, 205c are driven and signals therefrom are processed by the image element drive and processing circuits 206a, 206c.

Further, LEDs 207a, 207c for illumination are disposed around the objective lenses 204a, 204c, respectively. The LEDs 207a, 207c are driven by an LED drive circuit 208 provided in the central capsule body 202B.

Further, signals that were processed by the image element drive and the processing circuits 206a, 206c are sent to a transmission circuit 209 provided in the central capsule body 202B and are transmitted to the outside from an antenna (not shown in the figure). A battery 210 is also enclosed in the capsule body 202B. Energy such as electric current is supplied to the observation devices such as the image pickup elements 205a, 205c enclosed in the capsule bodies 202A and 202C by the battery 210.

Magnets 211a, 211c are provided inside the capsule bodies 202A, 202C on both end sides.

Figure 42:
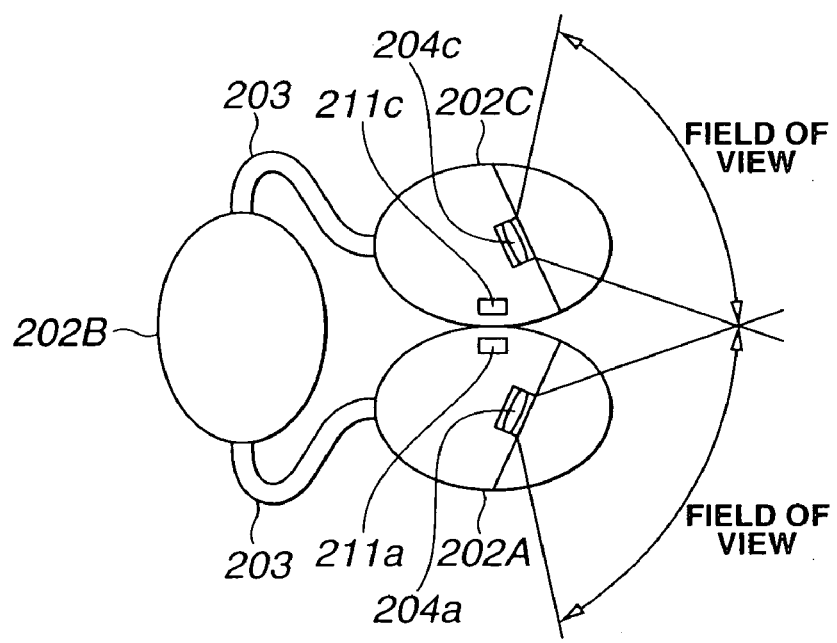
FIG. 42 explains the operation in a state in which two capsule bodies of the capsule-type endoscope of the third modification of the tenth embodiment of the present invention are combined.

Therefore, similarly to the case explained with reference to FIG. 38, if the capsule-type endoscope 201 reaches a wide portion such as a stomach, the capsule bodies 202A, 202C located on both end sides are attracted and combined by the magnets 211a, 211c, as shown in FIG. 42. Therefore, the two capsules are joined in the prescribed position.

In such a state, image pickup is possible within a wide range because of respective inclined fields of view. The operation and effect in this case are similar to those explained with reference to FIG. 37.

The present invention also covers embodiments composed, for example, by partial combinations of the above-described embodiments.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A system comprising:
   a swallowable capsule type medical device including:
   a first capsule type endoscope and a second capsule type endoscope connected to the first capsule type endoscope via a connection portion;
   a first image capturing device for capturing an image of an inside of a subject at a set image pickup cycle while illuminating at a set illumination interval, the first image capturing device being provided in the first capsule type endoscope;
   a second image capturing device for capturing an image of an inside of the subject by shifting a timing by a predetermined time period from a timing of the first image capturing device, at the set image pickup cycle while illuminating at the set illumination interval, the second image capturing device being provided in the second capsule type endoscope;
   a first transmitter for wirelessly transmitting the image captured by the first image capturing device to outside the subject; and
   a second transmitter for wirelessly transmitting the image captured by the second image capturing device to outside the subject,
   a portable external device including:
   a housing configured to be attached to the subject;
   a receiver disposed in or on the housing for receiving signals of the images wirelessly transmitted from the first transmitter and the second transmitter of the capsule type medical device;
   a signal processor contained in the housing and adapted to process the signals of the images wirelessly transmitted from the first transmitter and the second transmitter of the capsule type medical device;
   a control member which is controlled to change at least one of the illumination interval and the image pickup cycle set in the capsule type medical device after the capsule type medical device has started image-pickup;
   a third transmitter for wirelessly transmitting to the capsule type medical device a control signal of the at least one of the illumination interval and the image pickup cycle changed by operating the control member;
   a display portion contained in the housing and adapted to display the image processed by the signal processor, while the swallowable capsule type medical device is in an inside of the subject;
   a storage portion contained in the housing and adapted to store data of the image; and
   an output portion for downloading the data of the image stored in the storage portion to a terminal, after inspection by the capsule type medical device.

2. The system according to claim 1, wherein the portable external device further comprises a control portion adapted to transmit an instruction for performing a predetermined function to the swallowable capsule type medical device.

3. The system according to claim 1, wherein the housing is configured to be worn by the subject.

4. A method of displaying an image in a subject, comprising:
   capturing an image using a first image capturing device of a capsule type medical device which includes the first image capturing device and a second image capturing device and which is introduced into the subject at a set image pickup cycle while illuminating at a set illumination interval;
   capturing an image using the second image capturing device by shifting a timing by a predetermined time period from a timing of the first image capturing device, at the set image pickup cycle while illuminating at the set illumination interval;
   generating wireless signals of the images captured by the first and second image capturing devices and transmitting the wireless signals to an outside of the subject;
   receiving the wireless signals at a portable external device configured to be attached to the subject;
   processing the received signals with the external device;
   displaying the image based on the received signals, on a first display portion contained in the same housing as the external device, while the capsule type medical device is in an inside of the subject;
   changing, with a control member of the external device, at least one of the illumination interval and the image pickup cycle set in the capsule type medical device after the capsule type medical device has started image-pickup;
   wirelessly transmitting to the capsule type medical device a control signal of the at least one of the illumination interval and the image pickup cycle changed with the control member; and
   downloading data of an image stored in a storage portion of the external device to a terminal, after inspection by the capsule type medical device.

5. The method according to claim 4, further comprising storing data of the received image in a storage portion contained in the same housing as the external device.

6. The method according to claim 5, wherein the downloading comprises downloading data of the image stored in the storage portion into a terminal having a second display portion and the method further comprises displaying the image downloaded from the storage portion, on the second display portion.

7. The method according to claim 6, further comprising detachably connecting the terminal to the external device.

8. The method according to claim 4, further comprising securing the external device to the subject.

9. A system comprising:
   a swallowable capsule type medical device including:
   a first capsule type endoscope and a second capsule type endoscope connected to the first capsule type endoscope via a connection portion;
   a first image capturing device for capturing an image of an inside of a subject at a set image pickup cycle while illuminating at a set illumination interval, the first image capturing device being provided in the first capsule type endoscope;
   a second image capturing device for capturing an image of an inside of the subject by shifting a timing by a predetermined time period from a timing of the first image capturing device, at the set image pickup cycle while illuminating at the set illumination interval, the second image capturing device being provided in the second capsule type endoscope;
   a first transmitter for wirelessly transmitting the image captured by the first image capturing device to outside the subject: and
   a second transmitter for wirelessly transmitting the image captured by the second image capturing device to outside the subject;
   a portable external device including:
   a housing configured to be worn by the subject;
   a signal processor contained in the housing and adapted to process a signals of the images wirelessly transmitted from the first transmitter and the second transmitter of the capsule type medical device;

a control member which is controlled to change at least one of the illumination interval and the image pickup cycle set in the capsule type medical device after the capsule type medical device has started image-pickup;

a third transmitter for wirelessly transmitting to the capsule type medical device a control signal of the at least one of the illumination interval and the image pickup cycle changed by operating the control member;

a display portion contained in the housing and adapted to display the image processed by the signal processor, while the swallowable capsule type medical device is in an inside of the subject;

a storage portion contained in the housing and adapted to store data of the image; and an output portion for, after data of a plurality of images are stored in the storage portion, downloading the data of the plurality of images to a terminal, in a state where the portable external device is detached from the subject.

10. The system according to claim 9, wherein the portable external device further comprises a control portion adapted to transmit an instruction for performing a predetermined function to the swallowable capsule type medical device.

11. A method of displaying an image in a subject, comprising:

capturing an image using a first image capturing device of a capsule type medical device which includes the first image capturing device and a second image capturing device and which is introduced into the subject at a set image pickup cycle while illuminating at a set illumination interval;

capturing an image using the second image capturing device by shifting a timing by a predetermined time period from a timing of the first image capturing device, at the set image pickup cycle while illuminating at the set illumination interval;

generating wireless signals of the images captured by the first and second image capturing devices and transmitting the wireless signals to an outside of the subject;

securing a portable external device to the subject:

receiving the wireless signal at the outside of the subject;

processing the received signal with the external device;

changing, with a control member of the external device, at least one of the illumination interval and the image pickup cycle set in the capsule type medical device after the capsule type medical device has started image-pickup;

wirelessly transmitting to the capsule type medical device a control signal of the at least one of the illumination interval and the image pickup cycle changed by the control member;

displaying the image based on the received signal, on a first display portion contained in the same housing as the external device, while the capsule type medical device is in an inside of the subject; and after data of a plurality of images are stored in a storage portion in the external device, downloading the data of the plurality of images to a terminal, in a state where the portable external device is detached from the subject.

12. The method according to claim 11, further comprising storing data of the received image in a storage portion contained in the same housing as the external device.

13. The method according to claim 12, wherein the downloading comprises downloading data of the image stored in the storage portion into a terminal having a second display portion and the method further comprises displaying the image downloaded from the storage portion, on the second display portion.

14. The method according to claim 13, further comprising detachably connecting the terminal to the external device.

15. A method of displaying an image in a living body, the method comprising:

attaching to the living body an external unit including a recording portion capable of recoding an image, and having a capsule type medical device including a first image capturing device and a second image capturing device swallowed into the living body;

capturing an image of inside of a living body using the first image capturing device at a set image pickup cycle while illuminating at a set illumination interval;

capturing an image using the second image capturing device by shifting a timing by a predetermined time period from a timing of the first image capturing device, at a set image pickup cycle while illuminating at a set illumination interval;

transmitting the images captured by the first and second image capturing devices to outside of the living body by a wireless signal;

receiving the wireless signal by the external unit positioned outside the living body;

changing, with a control member of the external unit, at least one of the illumination interval and the image pickup cycle set in the capsule type medical device after the capsule type medical device has started image-pickup;

wirelessly transmitting to the capsule type medical device a control signal of the at least one of the illumination interval and the image pickup cycle changed by the control member;

displaying the received image on a first display portion in a state where the external unit is attached to the living body, while the capsule type medical device is in the inside of the subject;

storing a plurality of images by sequentially storing the received image in the recording portion provided to the external unit;

detaching the external unit from the living body and downloading to a terminal an image stored in the recording portion of the external unit; and after the downloading, displaying the image downloaded to the terminal on a second display portion.

16. The method according to claim 15, wherein the external unit is detachably connected to the terminal.

* * * * *